United States Patent
Jastifer

(10) Patent No.: US 10,893,933 B2
(45) Date of Patent: Jan. 19, 2021

(54) TISSUE ANCHORS, KITS, AND ASSOCIATED METHODS

(71) Applicant: James Jastifer, Vicksburg, MI (US)

(72) Inventor: James Jastifer, Vicksburg, MI (US)

(*) Notice: Subject to any disclaimer, the term of this patent is extended or adjusted under 35 U.S.C. 154(b) by 14 days.

(21) Appl. No.: 15/901,929

(22) Filed: Feb. 22, 2018

(65) Prior Publication Data

US 2018/0243078 A1  Aug. 30, 2018

Related U.S. Application Data

(60) Provisional application No. 62/462,962, filed on Feb. 24, 2017.

(51) Int. Cl.
*A61F 2/30* (2006.01)
*A61B 17/04* (2006.01)
(Continued)

(52) U.S. Cl.
CPC ........ *A61F 2/0811* (2013.01); *A61B 17/0401* (2013.01); *A61F 2/0095* (2013.01); *A61F 2/0805* (2013.01); *A61B 50/30* (2016.02); *A61B 2017/044* (2013.01); *A61B 2017/0414* (2013.01); *A61B 2017/0445* (2013.01); *A61F 2002/0829* (2013.01); *A61F 2002/0841* (2013.01); *A61F 2002/0852* (2013.01); *A61F 2002/0858* (2013.01); *A61F 2002/0882* (2013.01); *A61F 2002/0888* (2013.01); *A61F 2220/0033* (2013.01); *A61F 2220/0041* (2013.01);
(Continued)

(58) Field of Classification Search
CPC ........ A61B 17/0401; A61B 2017/0464; A61B 2017/0414; A61B 17/864; A61B 17/7032; A61B 17/8605; A61B 17/8685; A61B 2017/044; A61B 2017/0649; A61B 17/0469; A61B 2017/0412; A61B 2017/0427; A61B 2017/0445; A61B 17/8042; A61B 17/0642; A61B 17/68; A61B 17/7001; A61B 17/7035; A61F 2/0811; A61F 2002/0888; A61F 2210/0004; A61F 2002/0852; A61F 2002/0882; A61F 2002/30062; A61F 2/08; A61F 2/28; A61F 2002/30461; A61F 2002/3085; A61F 2002/0858; A61F 2002/087
See application file for complete search history.

(56) References Cited

U.S. PATENT DOCUMENTS 2,025,663 A   12/1935  Iuliano
2,075,508 A    3/1937  Davidson
(Continued)

FOREIGN PATENT DOCUMENTS

EP   2572648   3/2013
EP   2486856   7/2014
EP   2774546   9/2014

*Primary Examiner* — Ann Schillinger
(74) *Attorney, Agent, or Firm* — MacMillan, Sobanski & Todd, LLC

(57) ABSTRACT

Tissue anchors, kits that include a tissue anchor, and methods of anchoring tissue to a bone are described. An example embodiment of a tissue anchor includes a screw and a stem releasably attached to the screw. The screw defines a first opening, a second opening, and a lumen that extends from the first opening to the second opening. A portion of the stem is sized and configured to be received within the lumen defined by the screw.

20 Claims, 16 Drawing Sheets

(51) Int. Cl.
   *A61B 17/58* (2006.01)
   *A61F 2/08* (2006.01)
   *A61F 2/00* (2006.01)
   *A61B 50/30* (2016.01)

(52) U.S. Cl.
   CPC ............... *A61F 2230/0067* (2013.01); *A61F 2250/0039* (2013.01); *A61F 2250/0064* (2013.01); *A61F 2250/0087* (2013.01)

(56) References Cited

U.S. PATENT DOCUMENTS

| | | |
|---|---|---|
| 2,543,056 A | 2/1951 | Pollack et al. |
| 3,409,014 A | 11/1968 | Shannon |
| 5,100,405 A | 3/1992 | McLaren |
| 5,152,790 A | 10/1992 | Rosenberg et al. |
| 5,156,616 A | 10/1992 | Meadows et al. |
| 5,306,290 A | 4/1994 | Martins et al. |
| 5,370,662 A | 12/1994 | Stone et al. |
| 5,411,523 A | 5/1995 | Goble |
| 5,456,685 A | 10/1995 | Huebner |
| 5,486,197 A | 1/1996 | Le et al. |
| 5,534,011 A | 7/1996 | Greene, Jr. et al. |
| 5,545,180 A | 8/1996 | Le et al. |
| 5,643,320 A | 7/1997 | Lower et al. |
| 5,702,397 A * | 12/1997 | Goble ............... A61B 17/0401 606/232 |
| 5,720,766 A | 2/1998 | Zang et al. |
| 5,725,377 A | 3/1998 | Lemler et al. |
| 5,733,307 A | 3/1998 | Dinsdale |
| 6,027,523 A | 2/2000 | Schmieding |
| 6,264,677 B1 | 7/2001 | Simon et al. |
| 6,319,270 B1 | 11/2001 | Grafton et al. |
| 6,432,123 B2 | 8/2002 | Schwartz et al. |
| 6,461,373 B2 | 10/2002 | Wyman et al. |
| 6,685,728 B2 | 2/2004 | Sinnott et al. |
| 6,840,953 B2 | 1/2005 | Martinek |
| 6,916,321 B2 | 7/2005 | TenHuisen et al. |
| 7,116,794 B2 | 10/2006 | Westerkull |
| 7,150,757 B2 | 12/2006 | Fallin et al. |
| 7,329,272 B2 | 2/2008 | Burkhart et al. |
| 7,517,357 B2 | 4/2009 | Abrams et al. |
| 7,556,638 B2 | 7/2009 | Morgan et al. |
| 7,588,587 B2 | 9/2009 | Barbieri et al. |
| 7,637,926 B2 | 12/2009 | Foerster et al. |
| 7,678,134 B2 | 3/2010 | Schmieding et al. |
| 7,828,820 B2 | 11/2010 | Stone et al. |
| 7,875,058 B2 | 1/2011 | Holmes, Jr. |
| 7,883,529 B2 | 2/2011 | Sinnott et al. |
| 7,938,847 B2 | 5/2011 | Fanton et al. |
| 8,202,295 B2 | 6/2012 | Kaplan |
| 8,231,654 B2 | 7/2012 | Kaiser et al. |
| 8,277,484 B2 | 10/2012 | Barbieri et al. |
| 8,382,772 B2 | 2/2013 | Rotella et al. |
| 8,460,379 B2 | 6/2013 | Albertorio et al. |
| 8,663,279 B2 | 3/2014 | Burkhart et al. |
| 8,738,144 B2 | 5/2014 | Schneider |
| 8,771,315 B2 | 7/2014 | Lunn et al. |
| 8,821,541 B2 | 9/2014 | Dreyfuss et al. |
| 2002/0147463 A1 | 10/2002 | Martinek |
| 2003/0120309 A1 | 6/2003 | Colleran et al. |
| 2005/0090827 A1 | 4/2005 | Gedebou |
| 2006/0100630 A1 | 5/2006 | West, Jr. |
| 2006/0106423 A1 | 5/2006 | Weisel et al. |
| 2006/0282082 A1 | 12/2006 | Fanton et al. |
| 2007/0255317 A1 | 11/2007 | Fanton et al. |
| 2008/0004659 A1 | 1/2008 | Burkhart et al. |
| 2009/0312776 A1 | 12/2009 | Kaiser et al. |
| 2010/0125297 A1 | 5/2010 | Guederian et al. |
| 2011/0276092 A1 | 11/2011 | Dreyfuss |
| 2012/0059384 A1 | 3/2012 | Fan et al. |
| 2012/0203340 A1 | 8/2012 | Choinski et al. |
| 2012/0271416 A1 | 10/2012 | Mackay |
| 2013/0023928 A1 | 1/2013 | Dreyfuss |
| 2013/0096611 A1 | 4/2013 | Sullivan |
| 2013/0131733 A1 | 5/2013 | Chien et al. |
| 2013/0204297 A1 | 8/2013 | Melsheimer et al. |
| 2013/0261663 A1 | 10/2013 | Bittenson |
| 2014/0257384 A1 | 9/2014 | Dreyfuss et al. |
| 2014/0257385 A1 | 9/2014 | Lunn et al. |
| 2014/0277130 A1 | 9/2014 | Housman |
| 2015/0018878 A1* | 1/2015 | Rizk ............... A61B 17/0401 606/232 |
| 2015/0018947 A1 | 1/2015 | Barwood |
| 2015/0032157 A1 | 1/2015 | Dooney, Jr. et al. |
| 2015/0272567 A1* | 10/2015 | Feezor ............... A61B 17/0485 606/232 |

\* cited by examiner

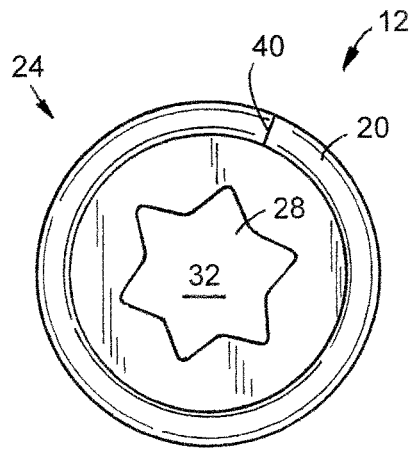
FIG.1
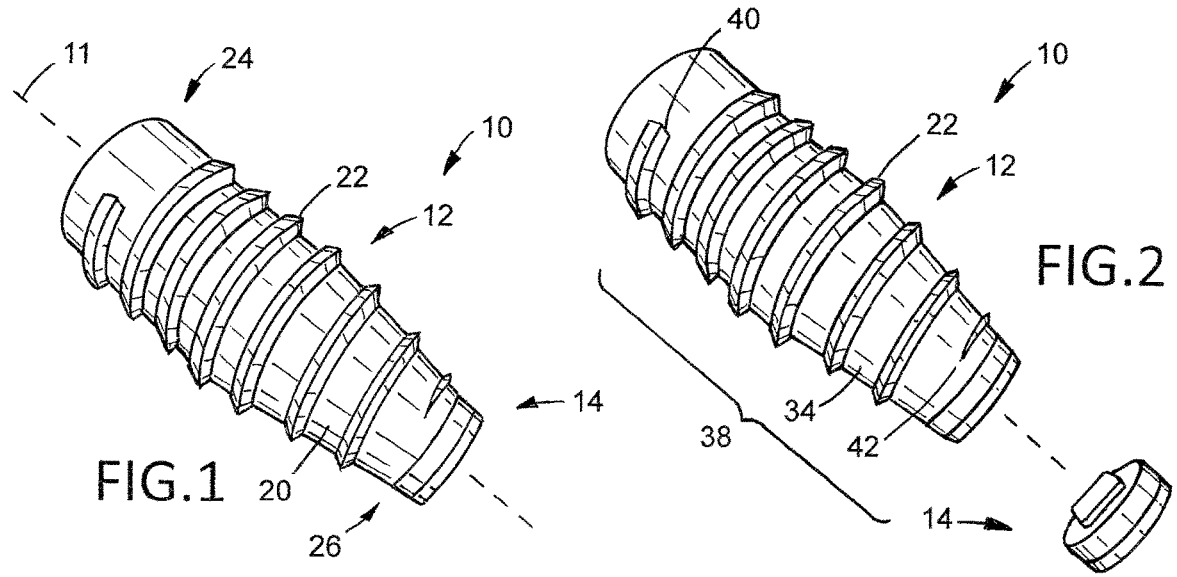
FIG.2
FIG.3
FIG.4

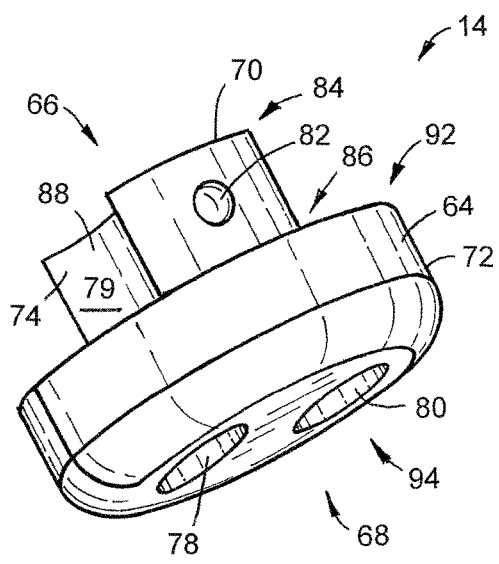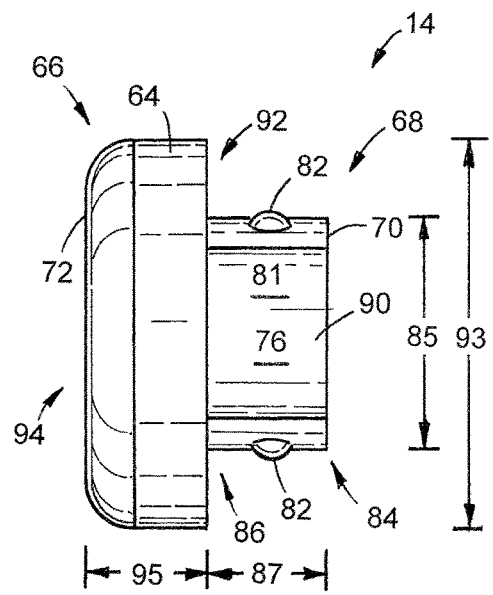
FIG.5  FIG.6
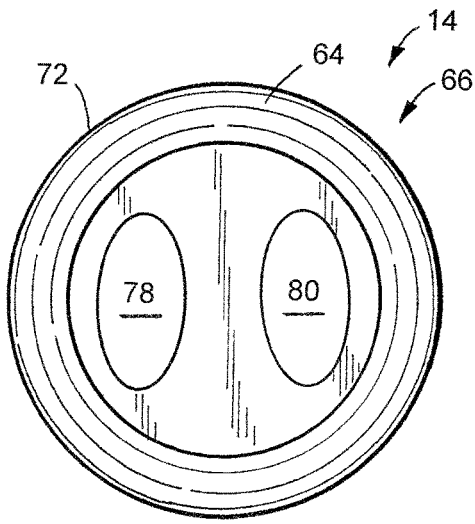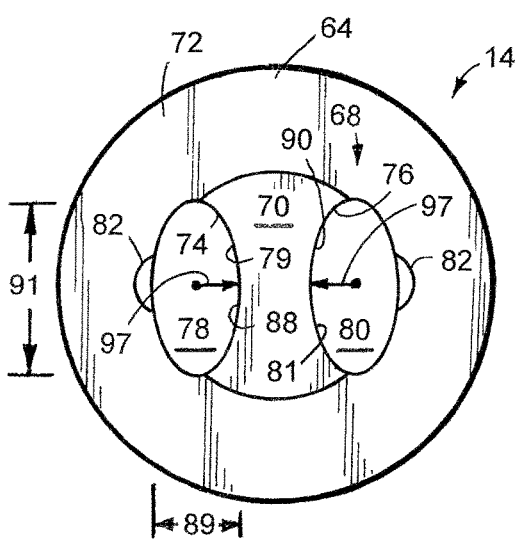
FIG.7  FIG.8

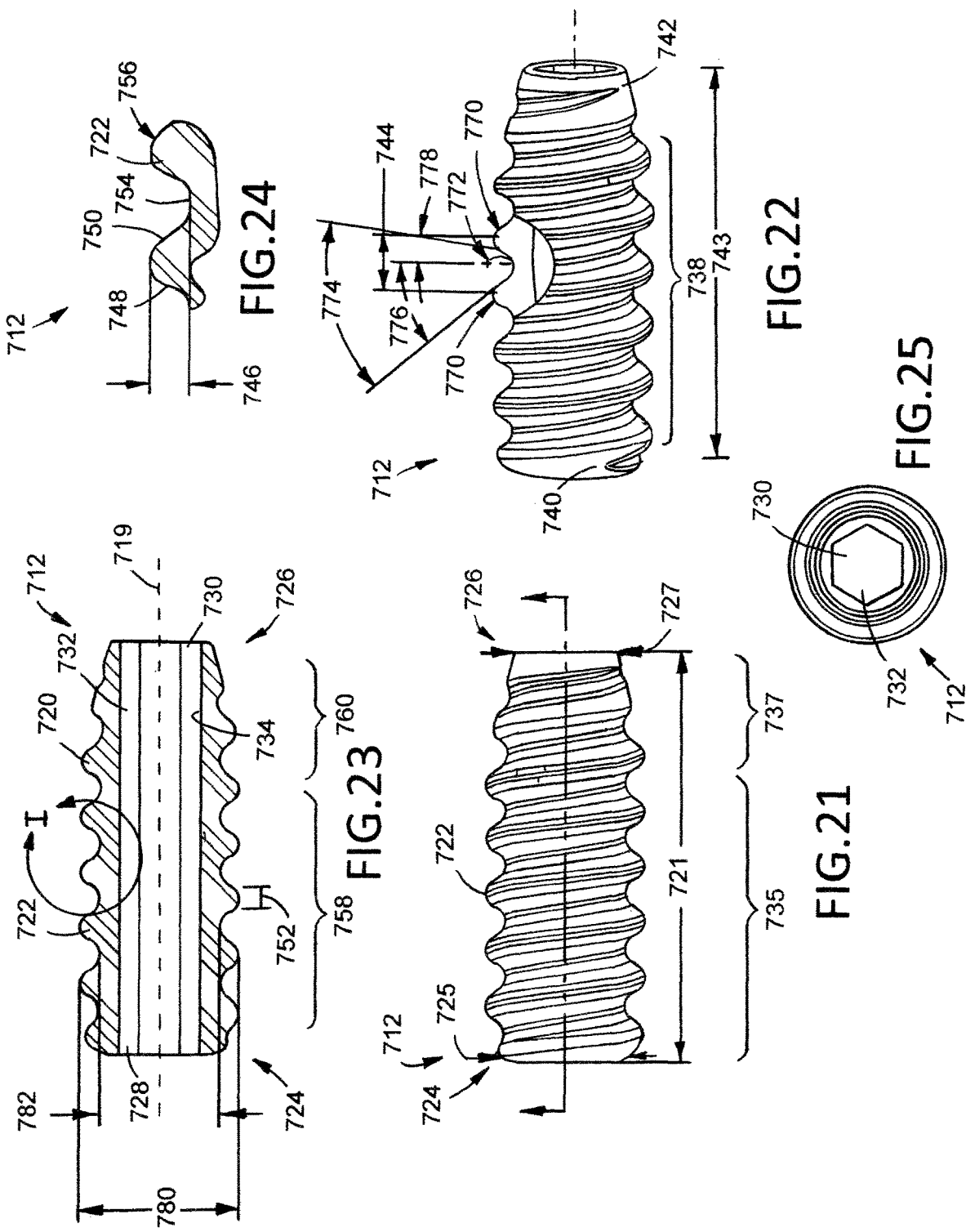

TISSUE ANCHORS, KITS, AND ASSOCIATED METHODS

FIELD

The disclosure relates generally to the field of medical devices. More particularly, the disclosure relates to tissue anchors, kits that include a tissue anchor, and methods of anchoring tissue to a bone.

BACKGROUND

Soft tissue, such as a ligament or tendon, sometimes becomes detached from the bone to which it was originally attached resulting in a loss, or decrease, of the tissue's functionality. Various devices have been developed to accomplish reattachment of tissue to bone, such as staples, screws, suture anchors, and interference screws. However, these devices only provide a single mechanism for attaching tissue to bone. For example, interference screws accomplish attachment between tissue and bone by advancing the screw into the bone while the tissue is positioned adjacent to the screw. However, depending on the structural arrangement of the thread of the interference screw, the tissue can be damaged by the thread as it is advanced into the bone, resulting in tearing and an increase in the potential for the tissue to become detached from the bone. Suture anchors accomplish attachment by passing a suture through a selected portion of the tissue and fixing the suture to the bone with a fastener. The suture is generally fixed to the tissue by tying it in a knot around the tissue, which can be complex and time consuming if access to the surgical site is limited.

Therefore, a need exists for new and useful approaches to attaching tissue to a bone.

SUMMARY OF SELECTED EXAMPLE EMBODIMENTS

Various tissue anchors, kits that include a tissue anchor, and methods of anchoring tissue to a bone are described herein.

An example tissue anchor includes a screw and a stem. The screw has a lengthwise axis, a screw main body, and a thread that extends from the screw main body and away from the lengthwise axis. The screw main body defines a first opening, a second opening, and a lumen that extends from the first opening to the second opening. The stem is releasably attached to the screw and partially disposed within the lumen defined by the screw. The stem has a stem main body that defines a first portion, a second portion, a first recess, a second recess, a first passageway, and a second passageway. The first portion of the stem has a first outside diameter, a first side, and a second side. The second portion of the stem has a second outside diameter that is greater than the first outside diameter. Each of the first and second recesses is defined on the first portion of the stem. The first recess is positioned on the first side of the first portion and the second recess is positioned on the second side of the first portion. Each of the first and second passageways extends through the second portion and is in communication with the lumen defined by the screw.

Another example tissue anchor includes a screw and a stem. The screw has a lengthwise axis, a screw main body, and a thread that extends from the screw main body and away from the lengthwise axis. The screw main body has a screw proximal end, a screw distal end, a distal portion that extends from the screw distal end toward the screw proximal end, a first outside diameter at the screw proximal end, and defines a first opening, a second opening, and a lumen that extends from the first opening to the second opening. The outside diameter of the screw main body tapers along the distal portion of the main body. The thread has a thread proximal end, a thread distal end, a thread length that extends from the thread proximal end to the thread distal end, a first portion that extends from the thread proximal end toward the thread distal end, a second portion that extends from the first portion of the thread to the thread distal end, a pitch, and a height. The pitch is constant along the thread length. The height is constant along the first portion of the thread and tapers along the second portion of the thread. The stem is releasably attached to the screw and partially disposed within the lumen defined by the screw. The stem has a stem main body that defines a first portion, a second portion, a first recess, a second recess, a first passageway, and a second passageway. The first portion of the stem has a first outside diameter, a first side, and a second side. The second portion of the stem has a second outside diameter that is greater than the first outside diameter. Each of the first and second recesses is defined on the first portion of the stem. The first recess is positioned on the first side of the first portion and the second recess is positioned on the second side of the first portion. Each of the first and second passageways extends through the second portion and is in communication with the lumen defined by the screw.

Another example tissue anchor includes a screw and a stem. The screw has a lengthwise axis, a screw main body, and a thread that extends from the screw main body and away from the lengthwise axis. The screw main body has a screw proximal end, a screw distal end, a distal portion that extends from the screw distal end toward the screw proximal end, a first outside diameter at the screw proximal end, and defines a first opening, a second opening, and a lumen that extends from the first opening to the second opening. The outside diameter of the screw main body tapers along the distal portion of the screw main body. The thread has a thread proximal end, a thread distal end, a thread length that extends from the thread proximal end to the thread distal end, a first portion that extends from the thread proximal end toward the thread distal end, a second portion that extends from the first portion of the thread to the thread distal end, a pitch, a height, a crest, a first side, a second side, and a thickness that extends from the first side of the thread to the second side of the thread. The pitch is constant along the thread length. The height is constant along the first portion of the thread and tapers along the second portion of the thread. The crest is blunted along a portion of the thread. The thickness of the thread is constant along the first portion of the thread and tapers along the second portion of the thread. The stem is releasably attached to the screw and partially disposed within the lumen defined by the screw. The stem has a stem main body defining a first portion, a second portion, a first recess, a second recess, a first passageway, and a second passageway. The first portion of the stem has a first outside diameter, a first side, and a second side. The second portion of the stem has a second outside diameter that is greater than the first outside diameter. Each of the first and second recesses is defined on the first portion of the stem. The first recess is positioned on the first side of the first portion and the second recess is positioned on the second side of the first portion. Each of the first and second passageways extends through the second portion and is in communication with the lumen defined by the screw. The first passageway is disposed adjacent to the first recess. The second passageway is disposed adjacent to the second recess.

An example kit that includes a tissue anchor includes a first tissue anchor according to an embodiment; a second tissue anchor according to an embodiment; a third tissue anchor according to an embodiment; a storage container; and instructions for use.

An example method of anchoring tissue to a bone comprises the steps of: creating an opening over the tissue intended to be anchored to a bone; locating the tissue; trimming a portion of the tissue; selecting a tissue anchor; drilling a passageway into a bone; reaming the passageway to a desired diameter based on the diameter of the selected tissue anchor; advancing a portion of the tissue into the passageway such that a portion of the tissue is disposed within the passageway; introducing the screw of the selected tissue anchor into the passageway containing a portion of the tissue such that a portion of the tissue disposed within the passageway is disposed adjacent to the distal portion of the screw; advancing the screw such into the passageway such that the tissue is anchored between the screw and the bone; closing the opening.

Another example method of anchoring tissue to a bone comprises the steps of: creating an opening over the tissue intended to be anchored to a bone; locating the tissue; selecting a tissue anchor; drilling a passageway into a bone; passing the first end of the suture through the lumen defined by the screw and the first passageway defined by the stem; passing the first end of the suture through the second passageway defined by the stem and through the lumen defined by the screw such that the first and second ends of the suture are disposed outside of the screw; introducing the screw of the selected tissue anchor into the passageway such that a portion of the tissue anchor is disposed within the passageway; advancing the screw into the passageway such that the screw is anchored to the bone; positioning a portion of the tissue adjacent the tissue anchor; attaching the tissue to the screw using the suture such that the tissue is anchored to the screw; closing the opening.

Another example method of anchoring tissue to a bone comprises the steps of: creating an opening over the tissue intended to be anchored to a bone; locating the tissue; trimming a portion of the tissue; selecting a tissue anchor; drilling a passageway into a bone; advancing a portion of the tissue into the passageway such that a portion of the tissue is disposed within the passageway; introducing the screw of the selected tissue anchor into the passageway such that a portion of the tissue anchor is disposed within the passageway; passing the first end of the suture through the lumen defined by the screw and the first passageway defined by the stem; passing the first end of the suture through the second passageway defined by the stem and through the lumen defined by the screw such that the first and second ends of the suture are disposed outside of the screw; advancing the screw into the passageway such that the tissue is anchored between the screw and the bone; positioning a portion of the tissue adjacent the tissue anchor; attaching the tissue to the screw using the suture such that the tissue is anchored to the screw; closing the opening.

Additional understanding of the example tissue anchors, kits that include a tissue anchor, and methods of anchoring tissue to a bone can be obtained by review of the detailed description, below, and the appended drawings.

BRIEF DESCRIPTION OF THE DRAWINGS

FIG. 1 is a perspective view of an example tissue anchor.

FIG. 2 is an exploded perspective view of the tissue anchor illustrated in FIG. 1.

FIG. 3 is a top view of the screw of the tissue anchor illustrated in FIG. 1.

FIG. 4 is a cross-sectional view of the screw of the tissue anchor illustrated in FIG. 1 taken along the lengthwise axis of the screw.

FIG. 5 is a perspective view of the stem of the tissue anchor illustrated in FIG. 1.

FIG. 6 is a side view of the stem of the tissue anchor illustrated in FIG. 1.

FIG. 7 is a bottom view of the stem of the tissue anchor illustrated in FIG. 1.

FIG. 8 is a top view of the stem of the tissue anchor illustrated in FIG. 1.

FIG. 21 is a side view of a first alternative screw that can be included in a tissue anchor.

FIG. 22 is a partial perspective view of the screw illustrated in FIG. 21.

FIG. 23 is a cross-sectional view of the screw illustrated in FIG. 21 taken along the lengthwise axis of the screw.

FIG. 24 is a magnified view of area I indicated in FIG. 23.

FIG. 25 is a bottom view of the screw illustrated in FIG. 21.

DETAILED DESCRIPTION

Figure 9:
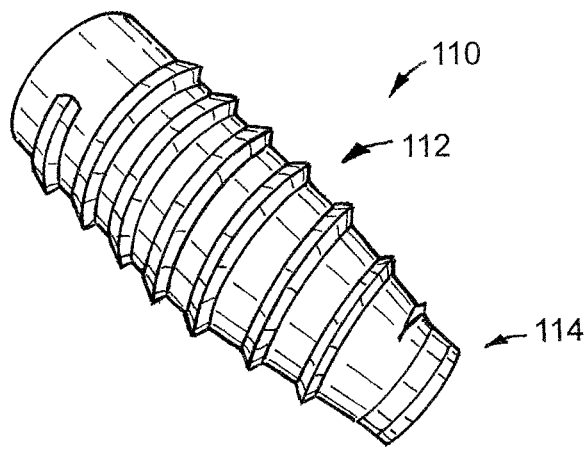
FIG. 9 is a perspective view of a second example tissue anchor.
Figure 10:
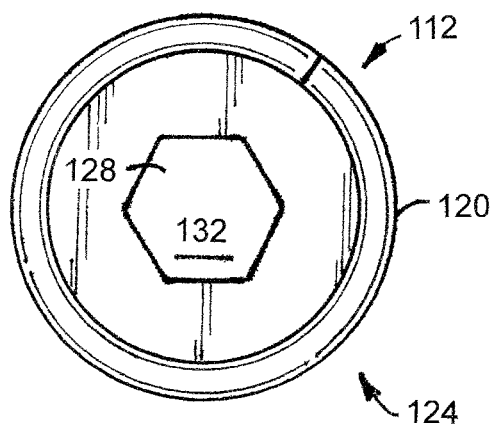
FIG. 10 is a top view of the screw of the tissue anchor illustrated in FIG. 9.
Figure 11:
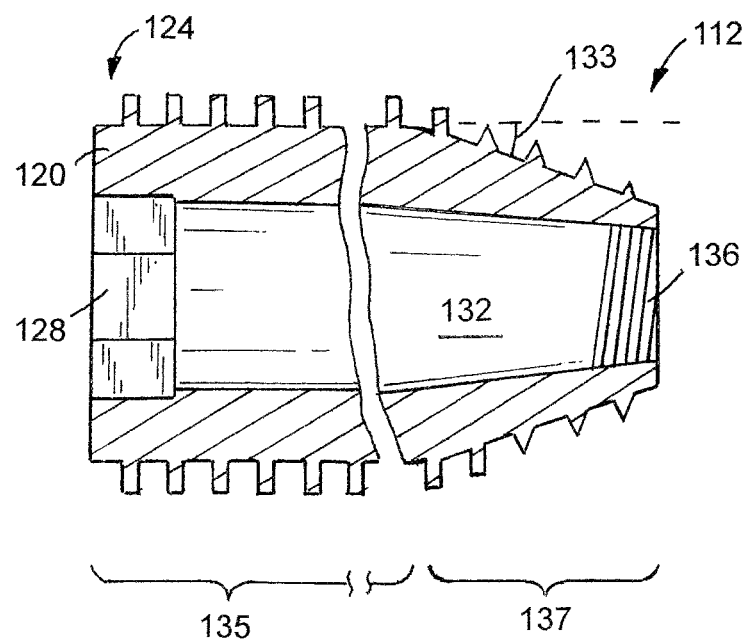
FIG. 11 is a cross-sectional view of the screw of the tissue anchor illustrated in FIG. 9 taken along the lengthwise axis of the screw.
Figure 12:
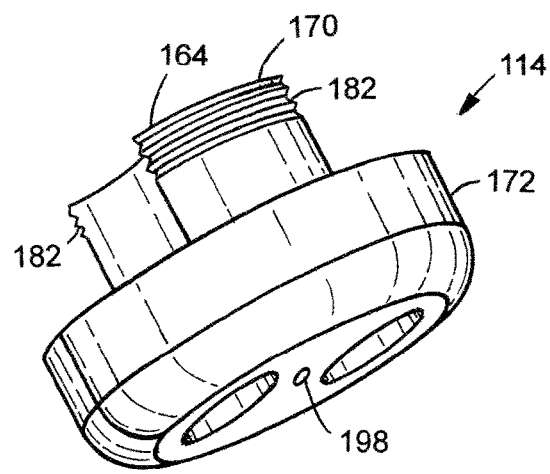
FIG. 12 is a perspective view of the stem of the tissue anchor illustrated in FIG. 9.
Figure 13:
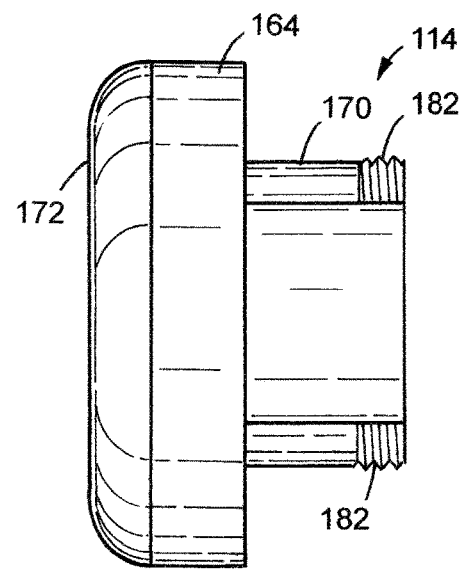
FIG. 13 is a side view of the stem of the tissue anchor illustrated in FIG. 9.
Figure 14:
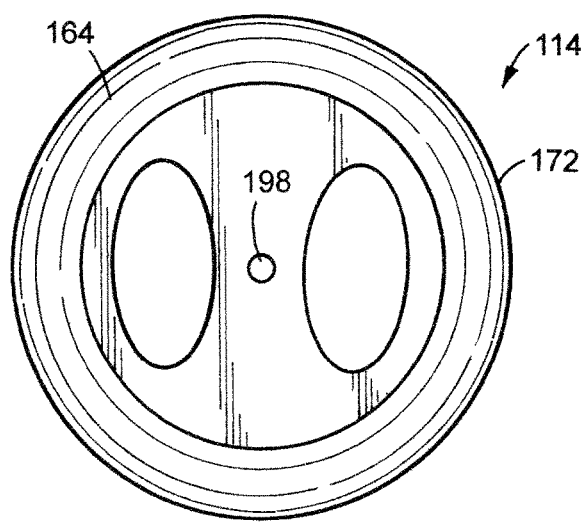
FIG. 14 is a bottom view of the stem of the tissue anchor illustrated in FIG. 9.
Figure 15:
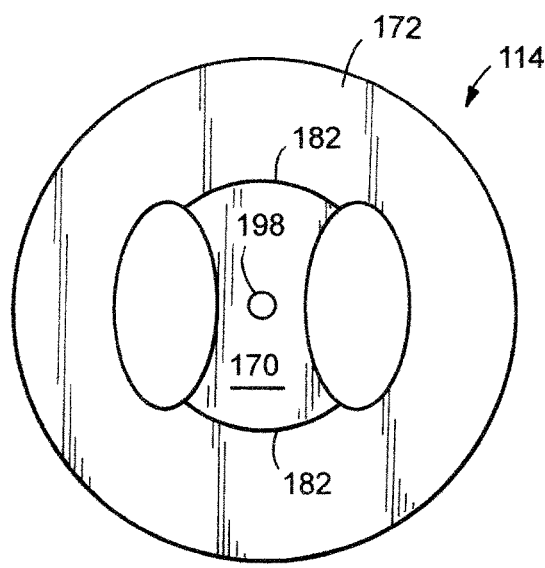
FIG. 15 is a top view of the stem of the tissue anchor illustrated in FIG. 9.

The following detailed description and the appended drawings describe and illustrate various example embodiments of tissue anchors, kits that include a tissue anchor, and methods of anchoring tissue to a bone. The description and illustration of these examples are provided to enable one skilled in the art to make and use a tissue anchor, to make a kit that includes a tissue anchor, and to practice a method of anchoring tissue to a bone. They are not intended to limit the scope of the claims in any manner.

FIGS. 1, 2, 3, 4, 5, 6, 7, and 8 illustrate a first example tissue anchor 10. The tissue anchor 10 includes a lengthwise axis 11, a screw 12, and a stem 14 releasably attached to the screw 12.

In the illustrated embodiment, the screw 12 has a lengthwise axis 19, a screw main body 20 and a thread 22. The screw main body 20 has a screw length 21, a screw proximal end 24, a first outside diameter 25, a screw distal end 26, a second outside diameter 27, and defines a first opening 28, a second opening 30, a lumen 32, a wall 34, a recess 36, a proximal portion 35, and a distal portion 37. The screw length 21 extends from the screw proximal end 24 to the screw distal end 26. The proximal portion 35 extends from the screw proximal end 24 toward the screw distal end 26. The distal portion 37 extends from the screw distal end 26 toward the screw proximal end 24. In the illustrated embodiment, the distal portion 37 extends from the proximal portion 35 to the screw distal end 26.

The first outside diameter 25 is disposed at the screw proximal end 24 and the second outside diameter 27 is disposed at the screw distal end 26. In the illustrated embodiment, the outside diameter of the screw main body 20 tapers along the distal portion 37 of the screw main body 20 such that a portion of the distal portion 37 of the screw main body 20 is disposed at an angle 33 relative to a plane that extends along the screw main body 20 from the screw proximal end 24 to the location that the proximal portion 35 meets the distal portion 37. In the illustrated embodiment, the angle 33 is equal to about 30 degrees.

The first opening 28 is defined at the screw proximal end 24 and the second opening 30 is defined at the screw distal end 26. The first opening 28 is sized and configured to receive a portion of a star drive to accomplish advancement of the screw into a portion of a body (e.g., bone). The second opening 30 is sized and configured to receive a portion of the stem 14. The lumen 32 extends from the first opening 28 to the second opening 30 and is sized and configured to receive one or more portions (e.g., lengths) of a suture and has a constant diameter along its length, except for the portions that include the first opening 28 and the recess 36. The wall 34 extends from the screw proximal end 24 to the screw distal end 26 and has a thickness along the screw length 21 such that no openings extend through the wall 34 and provide access to the lumen 32. As best shown in FIG. 4, the recess 36 is defined within the lumen 32 of the screw 12, extends into the wall 34, and is positioned, sized, and configured to receive the projections 82 defined by the stem 14 such that a snap-fit attachment between the screw 12 and the stem 14 can be accomplished.

While the first opening 28 has been illustrated as sized and configured to receive a portion of a star drive and the second opening 30 has been illustrated as sized and configured to receive a portion of the stem 14, the first opening defined on a screw can be sized and configured to receive a portion of any suitable tool and a second opening can be sized and configured to receive any suitable portion of a stem. Selection of a suitable size and configuration to form a first opening and/or a second opening defined by the screw main body can be based on various considerations, including the material that forms the screw. Examples of sizes and configurations considered suitable to form a first opening defined on a screw include those that are sized and configured to receive a portion of a handheld, or mechanically driven, driver, such as star (torx) driver, slotted driver, phillips head driver, allen wrench driver, Robertson driver, hex driver, and any other size and configuration considered suitable for a particular embodiment. Examples of sizes and configurations considered suitable to form a second opening defined on a screw include those that are sized and configured to receive a portion of a stem, a portion of a first portion of a stem, a portion of a second portion of a stem, a portion of a first portion and a portion of a second portion of a stem, and any other size and configuration considered suitable for a particular embodiment.

While the lumen 32 has been illustrated as having a constant diameter along its length, except for the portions that include the first opening 28 and the recess 36, a lumen defined by the screw main body can have any suitable diameter and selection of a suitable diameter for a lumen defined on a screw can be based on various considerations, including the size and configuration of the material intended to be passed through the lumen. Examples of diameters considered suitable for a lumen defined by the screw main body include diameters that are constant along a portion, or the entirety, of the length of the lumen, a first diameter along a proximal portion of a screw main body and a second diameter that tapers along a distal portion of the screw main body, a diameter that varies along the length of a screw, and any other configuration considered suitable for a particular embodiment.

Figure 26:
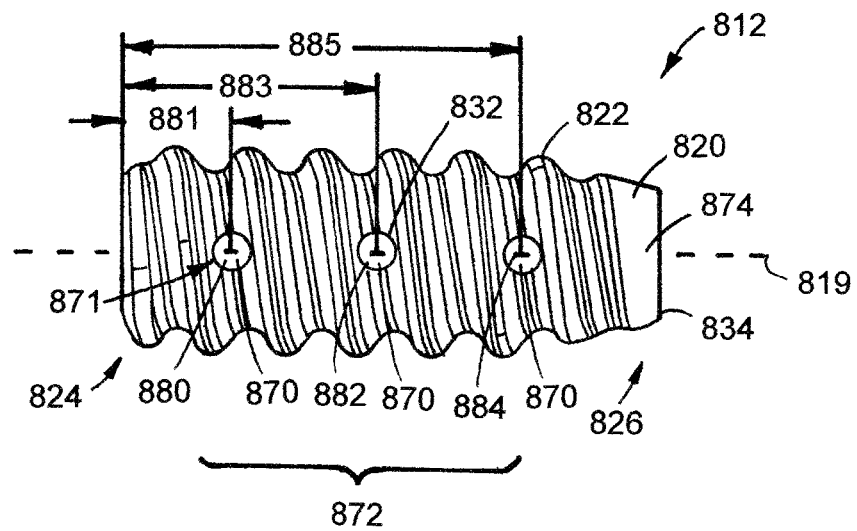
FIG. 26 is a side view of a second alternative screw that can be included in a tissue anchor.
Figure 27:
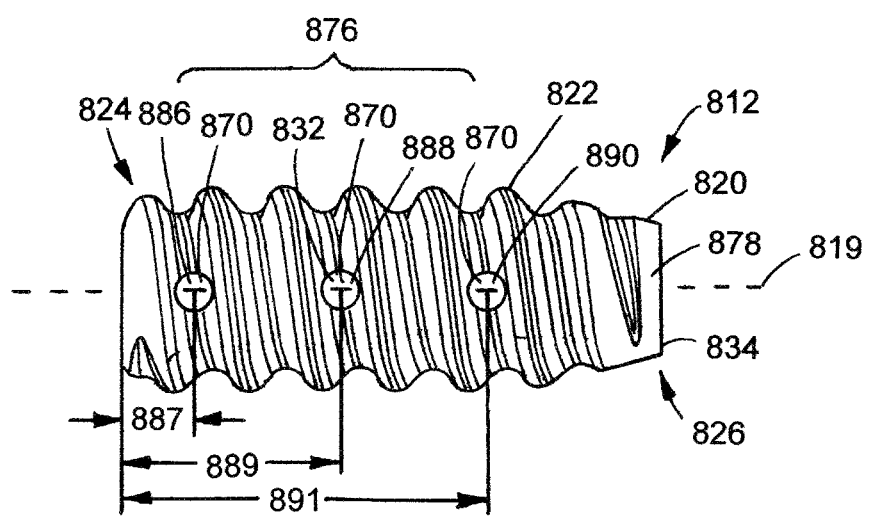
FIG. 27 is another side view of the screw illustrated in FIG. 26.

While the wall 34 has been illustrated as having a thickness along the screw length 21, a wall of a screw can have any configuration and selection of a suitable configuration for a wall of a screw can be based on various considerations, including the intended use of the screw. Examples of configurations considered suitable for a wall of a screw include those that are continuous and uninterrupted, define one or more passageway that extend from an outer surface to a lumen defined by the screw main body (e.g., to allow bone ingrowth), as shown in FIGS. 26 and 27, define one or more projections or roughed surfaces on a portion, or the entirety, of an outer surface or inner surface of the screw main body (e.g., to allow bone ingrowth), and any other configuration considered suitable for a particular embodiment.

While the outside diameter of the screw main body 20 has been illustrated as tapering along the distal portion 37 of the screw main body 20 such that a portion of the distal portion 37 of the screw main body 20 is disposed at an angle 33 relative to a plane that extends along the screw main body 20 from the screw proximal end 24 to the location the proximal portion 35 meets the distal portion 37, a screw main body can have any suitable outside diameter. Selection of a suitable outside diameter for a screw main body can be based on various considerations, including the structural arrangement of the portion of the body to which a tissue anchor is intended to be attached and/or the first outside diameter of the screw. Examples of outside diameters considered suitable for the screw main body include outside diameters that are constant along the screw length, that vary along the screw length, that taper from the screw proximal end to the screw distal end, that are constant along a first portion of a screw main body and that taper along a second portion of the screw main body, and any other outside diameter considered suitable for a particular embodiment. Examples of angles considered suitable between a proximal portion of a screw main body and a distal portion, or a portion of a distal portion, of a screw main body include angles equal to, greater than, less than, or about 15 degrees, about 30 degrees, about 45 degrees, about 60 degrees, and any other angle considered suitable for a particular embodiment. For example, a screw can have a first outside diameter that is equal to, or about, 8 millimeters and a second outside diameter that is equal to, or about, 4 millimeters such that a portion of a distal portion of the screw main body is disposed at an angle equal to, or about, 40 degrees relative to a plane that extends along the screw main body from the screw proximal end to the location that a proximal portion meets the distal portion. Alternatively, a screw can have a first outside diameter that is equal to, or about, 5 millimeters and a second outside diameter that is equal to, or about, 4 millimeters such that a portion of a distal portion of the screw main body is disposed at an angle equal to, or about, 10 degrees relative to a plane that extends along the screw main body from the screw proximal end to the location that a proximal portion meets the distal portion.

In the illustrated embodiment, the thread 22 extends from the screw main body 20, away from the lengthwise axis 19 of the screw 12, and is formed as an integral part of the screw 12. The thread 22 has a plurality of turns 38, a thread proximal end 40, a thread distal end 42, a thread length 43, a pitch 44, a height 46, a first side 48, a second side 50, a thickness 52, a root 54, a crest 56, a first portion 58, and a second portion 60.

The thread length 43 extends from the thread proximal end 40 to the thread distal end 42 and is less than the screw length 21. The first portion 58 extends from the thread proximal end 40 toward the thread distal end 42 and the second portion 60 extends from the first portion 58 to the thread distal end 42. The pitch 44 of the thread 22 is constant along the thread length 43. The height 46 of the thread 22 extends from the root 54 to the crest 56 and is constant along the first portion 58 of the of the thread 22 and tapers from the first portion 58 along the second portion 60 of the thread 22 to the thread distal end 42. The thickness 52 of the thread 22 extends from the first side 48 of the thread 22 to the second side 50 of the thread 22 at the root 54. The thickness 52 is constant along the first portion 58 of the thread 22 and tapers from the first portion 58 along the second portion 60 of the thread 22 to the thread distal end 42. In the illustrated embodiment, the crest 56 is blunted along the first portion 58 of the thread 22 and is pointed along the second portion 60 of the thread 22. The inclusion of a crest 56 that is blunted along a portion of the thread 22 is considered advantageous at least because it reduces the possibility of damaging tissue as the thread is advanced into a passageway and the tissue is secured between the thread and the wall defining the passageway (e.g., the wall defining a passageway created in a bone). This can be important because inclusion of a crest that defines a point along this portion can lead to tissue damage, including severing of the tissue, which could eliminate any anchoring provided by the tissue anchor.

While the thread 22 has been illustrated as having a thread length 43 that is less than the screw length 21, a pitch 44 that is constant along the thread length 43, a height 46 that is constant along the first portion 58 of the thread 22 and that tapers along the second portion 60 of the thread 22, and a thickness 52 that is constant along the first portion 58 of the thread 22 and that tapers along the second portion 60 of the thread 22, a thread included on a screw of a tissue anchor can have any suitable thread length, pitch, height, and thickness. Selection of a suitable thread length, pitch, height, and thickness for a thread included on a screw can be based on various considerations, including the material that forms the screw and/or thread. Examples of thread lengths considered suitable include thread lengths that are equal to, less than, greater than, or substantially equal to, the screw length. Examples of pitches considered suitable for a thread included on a screw include pitches that are constant, or varied, along the thread length, and any other pitch considered suitable for a particular embodiment. Examples of heights considered suitable for a thread included on a screw include heights that are constant, or varied, along the thread length, the first portion of the thread, or the second portion of the thread, constant along a first portion of a thread and that taper along a second portion of the thread, and any other height considered suitable for a particular embodiment. Examples of thicknesses considered suitable for a thread included on a screw include thicknesses that are constant, or varied, along the length of the thread, constant along a first portion of a thread and that taper along a second portion of the thread, and any other thickness considered suitable for a particular embodiment.

While the crest 56 has been illustrated as being blunted along the first portion 58 of the thread 22 and being pointed along the second portion 60 of the thread 22, a crest included on a screw can have any suitable structural arrangement. Selection of a suitable structural arrangement for a crest of a thread can be based on various considerations, including the intended use of a screw. Examples of structural arrangements considered suitable for the crest of a thread include those that are blunted, rounded, pointed, American National, British Standard, square, acme, buttress, or knuckle along a portion (e.g., first portion of the thread, second portion of the thread), or the entirety, of a thread, and any other structural arrangement considered suitable for a particular embodiment.

While the thread 22 has been illustrated as having a plurality of turns 38 that extends in a clockwise direction, a thread can include any suitable number of turns and selection of a suitable number of turns for a thread to define can be based on various considerations, such as the material that forms the portion of the body to which a tissue anchor is intended to be attached. Examples of numbers of turns considered suitable for a thread to define include a partial turn, one complete turn, at least one complete turn, two complete turns, a plurality of complete turns, and any other number considered suitable for a particular embodiment. Examples of directions considered suitable for a thread included on a screw to extend include in a clockwise direction or a counterclockwise direction relative to the lengthwise axis of a tissue anchor.

In the illustrated embodiment, the stem 14 is releasably attached to the screw 12 and has a stem main body 64. The stem main body 64 has a stem proximal end 66, a stem distal end 68, and defines a first portion 70, a second portion 72, a first recess 74, a second recess 76, a first passageway 78, a second passageway 80, and projections 82.

The first portion 70 is sized and configured to be received by the lumen 32 of the screw 12 such that the entirety of the first portion 70 is disposed within the lumen 32. The first portion 70 has a first portion proximal end 84, a first portion distal end 86, a first side 88, a second side 90, a first outside diameter 85, and a first portion length 87. The first portion 70 extends from the stem proximal end 66 toward the stem distal end 68. The first portion length 87 extends from the first portion proximal end 84 to the first portion distal end 86. The second portion 72 has a second portion proximal end 92 attached to the first portion 66, a second portion distal end 94, a second outside diameter 93, and a second portion length 95. The second portion 72 extends from the first portion 70 to the stem distal end 68. The second outside diameter 93 is greater than the first outside diameter 85. In the illustrated embodiment, the first outside diameter 85 is equal to about 0.055 inches. The second portion length 95 extends from second portion proximal end 92 to the second portion distal end 94 and is less than the first portion length 87. In the illustrated embodiment, the sum of the first portion length 87 and the second portion length 95 is equal to about 0.079 inches, the second portion length 95 is equal to about 0.049 inches, and a radius of curvature 96 equal to about 0.020 inches is defined on the second portion.

Each of the first and second recesses 74, 76 is defined on the first portion 70, extends into the stem main body 64, and extends from the first portion proximal end 84 to the first portion distal end 86. Each of the first and second recesses 74, 76 is disposed adjacent to a passageway 78, 80 defined by the second portion 72, has a radius of curvature 97, and is sized and configured to receive a portion of a suture. The first passageway 78 is disposed adjacent to the first recess 74 such that a first continuous surface 79 defines a portion of the first recess 74 and a portion of the first passageway 78. The second passageway 80 is disposed adjacent to the second recess 76 such that a second continuous surface 81 defines a portion of the second recess 76 and a portion of the second passageway 80. In the illustrated embodiment, the first continuous surface 79 is disposed from the second continuous surface 81 a distance equal to about 0.031 inches. The first recess 74 is positioned on the first side 88 of the first portion 70 and the second recess 76 positioned on a second side 90 of the first portion 70. In the illustrated embodiment, the radius of curvature 97 of the first recess is equal to the radius of curvature 97 of the second recess 76.

Each of the first and second passageways 78, 80 is defined on the second portion 72 of the stem 14 and extends through the second portion length 95. Each of the first and second passageways 78, 80 has an oval cross-sectional shape, is in communication with a recess 74, 76 defined on the first portion 70 of the stem 14, and is sized and configured to receive a portion of a suture, as described in more detail herein. In the illustrated embodiment, each of the first and second passageways 78, 80 has a length 89 equal to about 0.038 inches and a height 91 equal to about 0.065 inches. When the stem 14 is attached to the screw 12, each of the first and second passageways 78, 80 is in communication with the lumen 32 defined by the screw 12 such that the axes of the first and second passageways 78, 80 extend through the lumen 32. This configuration advantageously allows one or more portions of a suture to be passed through the lumen 32 defined by the screw 12 and through one, or both, of the passageways 78, 80.

Each of the projections 82 is defined on the first portion 70 of the stem 14 and extends from the first portion 70 and away from a lengthwise axis of the stem 14. A portion of each of the projections 82 is positioned, sized, and configured to be received within the recess 36 defined by the screw 12 such that the stem 14 can be releasably attached to the screw 12 using a snap-fit attachment.

While each of the recesses 74, 76 has been illustrated as having a radius of curvature, each of the passageways 78, 80 has been illustrated as having an oval cross-sectional shape, and each of the passageways 78, 80 has been illustrated as being in communication with the lumen 32 defined by the screw 12 such that the axes of the passageways 78, 80 extend through the lumen 32 when the stem 14 is attached to the screw 12, a recess and passageway defined on a stem can have any suitable structural arrangement. Selection of a suitable structural arrangement for a recess and/or passageway defined on a stem can be based on various considerations, including the size of the material intended to be disposed within the recess and/or passageway. Examples of structural arrangements considered suitable for a recess defined on a stem include those in which a first recess has a first radius of curvature and a second recess has a second radius of curvature that is equal to, different than, greater than, or less than, the first radius of curvature, a first recess has a first cross-sectional configuration (e.g., curved, linear, rectangular, square) and a second recess has a second cross-sectional configuration (e.g., curved, linear, rectangular, square) that is the same as, or different than, the first cross-sectional configuration, and any other structural arrangement considered suitable for a particular embodiment. Examples of cross-sectional shapes considered suitable to form a passageway defined on a stem include those that are circular, oval, square, rectangular, pentagonal, and any other cross-sectional shape considered suitable for a particular embodiment. Examples of positions considered suitable for one or more passageways defined by a stem include those in which each axis of two passageways extends through a lumen of a screw when a stem is attached to the screw, one axis of a passageway extends through a lumen of a screw when a stem is attached to the screw, no axis of a passageway extends through a lumen of a screw when a stem is attached to the screw, and any other position considered suitable for a particular embodiment. Examples of distances considered suitable to disposed a first continuous surface from a second continuous surface include distances equal to, greater than, less than, or about 0.031 inches, 0.032 inches, 0.030 inches, between about 0.025 inches and about 0.036 inches, and any other distance considered suitable for a particular embodiment. Examples of lengths and heights considered suitable for a passageway defined by a stem include lengths equal to, greater than, less than, or about 0.038 inches, 0.039 inches, 0.037 inches, between about 0.03 inches and about 0.05 inches, heights equal to, greater than, less than, or about 0.065 inches, 0.063 inches, 0.067 inches, between about 0.06 inches and about 0.07 inches, and any other length or height considered suitable for a particular embodiment.

While the first passageway 78 has been illustrated as being disposed adjacent to the first recess 74 such that a first continuous surface 79 defines a portion of the first recess 74 and a portion of the first passageway 78 and the second passageway 80 has been illustrated as being disposed adjacent to the second recess 76 such that a second continuous surface 81 defines a portion of the second recess 76 and a portion of the second passageway 80, any suitable structural arrangement between a recess and a passageway can be included on a stem. Selection of a suitable structural arrangement between a recess and a passageway can be based on various considerations, including the material that forms a stem. Examples of structural arrangements considered suitable between a recess and a passageway include those in which a continuous surface forms part, or the entirety, of a passageway and part, or the entirety, of a recess, a first surface forms a portion, or the entirety, of a recess and a second surface that is not continuous with the first surface forms a portion, or the entirety, of a passageway, and any other structural arrangement considered suitable for a particular embodiment.

While the entire first portion 70 has been illustrated as disposed within the lumen 32 when the stem 14 is releasably attached to the screw 12, any suitable portion of a stem can be disposed within a lumen defined by a screw. Selection of a suitable portion of a stem to position within a lumen defined by a screw when the stem is releasably attached to the screw can be based on various considerations, including the material that forms a stem and/or screw. Examples of portions of a stem considered suitable to position within a lumen defined by a screw when the stem is releasably attached to the screw include a portion, or the entirety, of the first portion, the second portion, the entire stem, and any other portion considered suitable for a particular embodiment.

While the second outside diameter 93 has been illustrated as being greater than the first outside diameter 85 and the second portion length 95 has been illustrated as being less than the first portion length 87, the first and second portions of a stem can have any suitable outside diameter and length. Selection of a suitable outside diameter and length for a first portion and/or second portion of a stem can be based on various considerations, including the structural arrangement of a screw intended to be used with the stem. Examples of configurations considered suitable for a stem include stems that have an outside diameter that is constant along a first portion and a second portion of the stem, a first outside diameter along a first portion and a second outside diameter along a second portion that is equal to, less than, greater than, or about the first outside diameter, stems that have a first length along a first portion and a second length along a second portion that is equal to, less than, greater than, or about the length of the first portion and any other configuration considered suitable for a particular embodiment. For example, a stem can have a second outside diameter that is equal to, or about, 4 millimeters. Examples of diameters considered suitable for a first outside diameter include those equal to, greater than, less than, or about 0.055 inches, between about 0.045 inches and about 0.065 inches, and any other diameter considered suitable for a particular embodiment. Examples of lengths considered suitable for a second portion length include those equal to, greater than, less than, or about 0.049 inches, between about 0.04 inches and about 0.06 inches, and any other length considered suitable for a particular embodiment. Examples of lengths considered suitable for a sum of a first portion length and a second portion length include those equal to, greater than, less than, or about 0.079 inches, between about 0.06 inches and about 0.1 inches, and any other length considered suitable for a particular embodiment. Examples of radii of curvature considered suitable to include on a second portion include those equal to, greater than, less than, or about 0.020 inches, between about 0.015 inches and 0.025 inches, and any other radius of curvature considered suitable for a particular embodiment.

A screw and stem included in a tissue anchor can be formed of any suitable material and selection of a suitable material to form a screw and a stem can be based on various considerations, including the intended use of the screw and stem. Examples of materials considered suitable to form a screw and/or stem include implant grade materials, biocompatible materials, materials that can be made biocompatible, metals such as stainless steel, titanium, metal alloys, nickel-titanium alloy (e.g., Nitinol), thermoplastics, polymers, polyetheretherketone (PEEK), Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, silicone, acrylonitrile butadiene styrene (ABS), polyoxymethylene (e.g., acetal), combinations of the materials described herein, and any other material considered suitable for a particular embodiment. In the illustrated embodiment, each of the screw 12 and stem 14 is formed of PEEK. Alternative embodiments, however, can include a screw that is formed of a first material and a stem that is formed of a second material that is different than the first material.

While the screw 12 has been illustrated as being attached to the stem 14 using a snap-fit attachment, a screw and a stem can be releasably attached to one another using any suitable technique or method of attachment. Selection of a technique or method of attachment considered suitable to accomplished attachment between a screw and a stem can be based on various considerations, including the material that forms the screw and/or stem. Examples of techniques and methods of attachment considered suitable to accomplished attachment between a screw and a stem include structures that accomplish a snap-fit attachment, press-fit attachment, interference fit attachment, friction fit attachment, threaded attachment, using an adhesive, fusing a screw to a stem, and any other technique or method considered suitable for a particular embodiment. Alternatively, a stem can be an integrated component of a screw such that they are formed as a continuous piece of material or a screw can be provided separately from a stem.

FIGS. 9, 10, 11, 12, 13, 14, and 15 illustrate another tissue anchor 110. The tissue anchor 110 is similar to the tissue anchor 10 illustrated in FIGS. 1, 2, 3, 4, 5, 6, 7, and 8 and described above, except as detailed below. The tissue anchor 110 includes a screw 112 and a stem 114 releasably attached to the screw 112.

In the illustrated embodiment, the first opening 128 is sized and configured to receive a portion of a hex drive to accomplish advancement of the screw 112 into a portion of a body and the angle 133 between a portion of the distal portion 137 and a plane that extends along the screw main body 120 from the screw proximal end 124 to the location the proximal portion 135 meets the distal portion 137 is equal to about 45 degrees. In addition, the screw 112 defines a thread 136 within the lumen 132 of the screw 112 that is positioned, sized, and configured to mate with a thread 182 defined by the stem 114 to achieve releasable attachment between the screw 112 and the stem 114.

In the illustrated embodiment, the stem main body 164 defines a third passageway 198. The third passageway 198 extends through both the first portion 170 and the second portion 172 of the stem 114, has a circular cross-sectional shape, and is sized and configured to receive a portion of a suture or guide wire, as described in more detail herein. In addition, the stem 114 defines a thread 182 that is positioned, sized, and configured to mate with the thread 136 defined by the screw 112 to achieve releasable attachment between the screw 112 and the thread 114.

While the third passageway 198 has been illustrated as having a circular cross-sectional shape, a passageway defined on a stem can have any suitable cross-sectional shape. Selection of a suitable cross-sectional shape for a passageway defined on a stem can be based on various considerations, including the size and configuration of the material intended to be disposed within a passageway. Examples of cross-sectional shapes considered suitable to form a passageway defined on a stem include those that are circular, oval, square, rectangular, pentagonal, and any other cross-sectional shape considered suitable for a particular embodiment.

Figure 16:
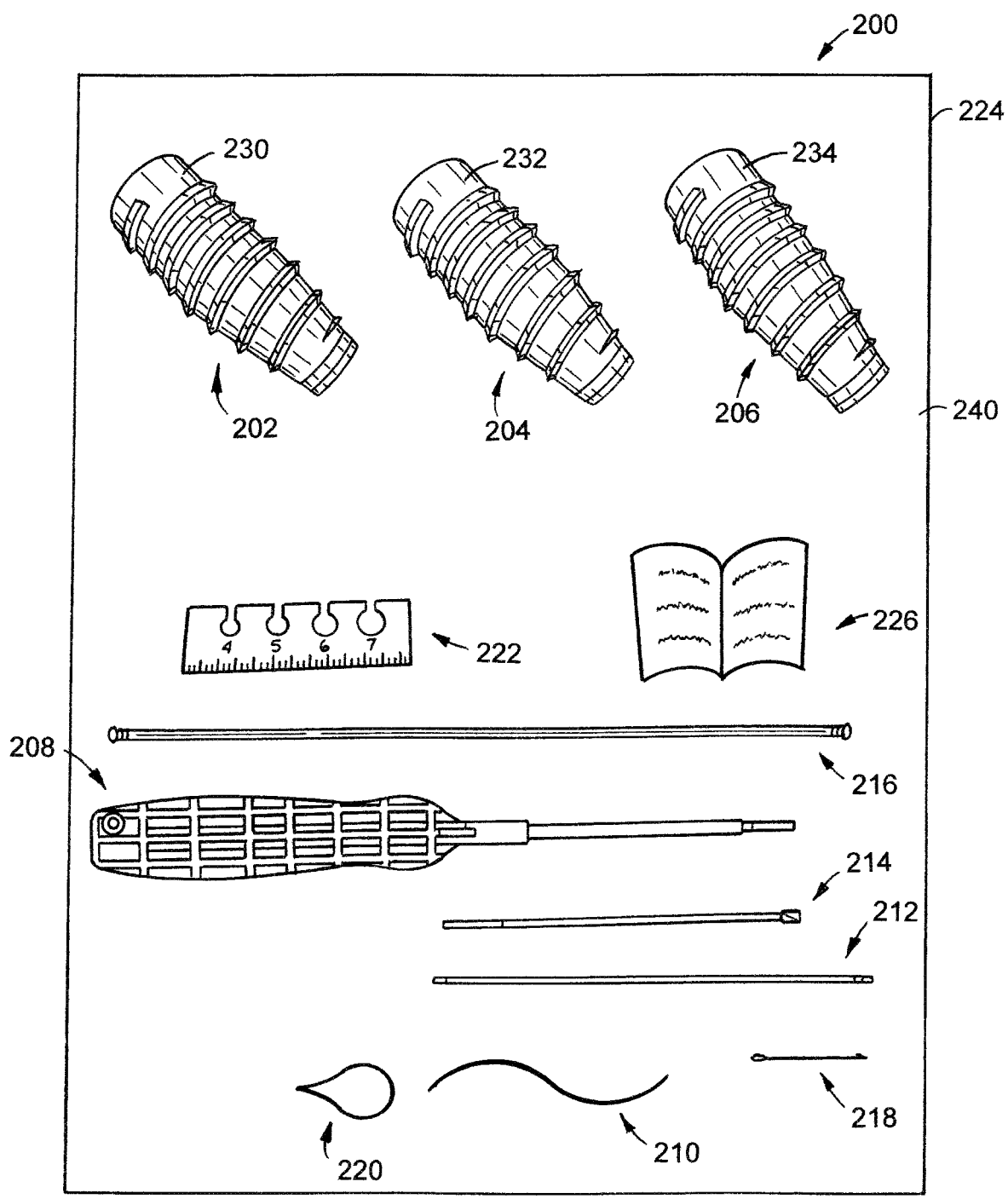
FIG. 16 illustrates an example kit that includes a plurality of tissue anchors.

FIG. 16 illustrates an exemplary kit 200 that includes a first tissue anchor 202 according to an embodiment, such as tissue anchor 10 illustrated in FIGS. 1, 2, 3, 4, 5, 6, 7, and 8; a second tissue anchor 204 according to an embodiment, such as tissue anchor 110 illustrated in FIGS. 9, 10, 11, 12, 13, 14, and 15; a third tissue anchor 206 according to an embodiment, such as tissue anchor 110 illustrated in FIGS. 9, 10, 11, 12, 13, 14, and 15; a tissue anchor driver 208; a suture 210; a drill bit 212, a reamer 214; a beath pin 216; a needle 218; a suture loop 220; a graft sizing block 222; a storage container 224; and instructions for use 226.

In the illustrated embodiment, the first tissue anchor 202 includes a material that has a first color 230, the second tissue anchor 204 includes a material that has a second color 232, and the third tissue anchor 206 includes a material that has a third color 234. The first color 230 is different than the second color 232 and the third color 234. The second color 232 is different than the first color 230 and the third color 234. The third color 234 is different than the first color 230 and the second color 232. The inclusion of multiple tissue anchors within a kit such that each tissue anchor includes a material that has a color that is different than the material included in the other tissue anchors is considered advantageous at least because it provides a user of the kit with a mechanism to determine which tissue anchor to use during a specific procedure without having to measure or otherwise identify the tissue anchor.

A tissue anchor can include a material that has any suitable color and the material can be included on any suitable portion of a tissue anchor using any suitable technique or method. Selection of a suitable color, location to include a material that has a color, and technique or method to include a material that has a color on a tissue anchor can be based on various considerations, including the material that forms the tissue anchor. Examples of colors considered suitable for a material included in a tissue anchor include blue, red, yellow, white, black, combinations of the colors described herein, and any other color considered suitable for a particular embodiment. Alternatively, one or more tissue anchors included in a kit can omit the inclusion of a material that has a color. Examples of locations considered suitable to include a material that has a color on a tissue anchor include on the screw, on the stem, on the entire screw, or a portion of the screw, on the entire stem, or a portion of the stem, on only the screw main body, on only the thread of the screw, on only the first portion of the stem, on only the second portion of the stem, and any other portion of a tissue anchor considered suitable for a particular embodiment. Examples of techniques and methods of including a material that has a color on a tissue anchor, or portion of a tissue anchor, include incorporating the material within the material that forms the tissue anchor, or a portion of the tissue anchor, applying the material using a tool (e.g., marker, paint brush), and any other technique or method considered suitable for a particular embodiment.

While kit 200 has been illustrated as including three tissue anchors 202, 204, 206, a tissue anchor driver 208, a suture 210, a drill bit 212, a reamer 214, a beath pin 216, a needle 218, a suture loop 220, a graft sizing block 222, a storage container 224, and instructions for use 226, a kit can include any suitable number, and type, of tissue anchors, screws, drivers, sutures, drill bits, reamers, beath pins, needles, suture loops, graft sizing blocks, storage containers, and/or instructions for use. Selection of a suitable number, and/or type, of tissue anchors, tissue anchor drivers, sutures, drill bits, reamers, beath pins, needles, suture loops, graft sizing blocks, storage containers, and/or instructions for use to include in a kit can be based on various considerations, such as the treatment intended to be performed. Examples of suitable numbers of tissue anchors, screws, drivers, sutures, drill bits, reamers, beath pins, needles, suture loops, graft sizing blocks, storage containers, and/or instructions for use to include in a kit include at least one, one, two, a plurality, three, four, five, six, and any other number considered suitable for a particular embodiment. Examples of tissue anchors and screws considered suitable to include in a kit include tissue anchor 10, tissue anchor 110, variations of the tissue anchors described herein, screw 712, screw 812, tissue anchors that include alternative screws, such as screw 712, and/or screw 812, and/or any other tissue anchor and/or screw considered suitable for a particular embodiment.

A tissue anchor driver, drill bit, reamer, and beath pin included in a kit can have any suitable structural arrangement and be formed of any suitable material and selection of a suitable structural arrangement and material to form a tissue anchor driver, a reamer, and a beath pin can be based on various considerations, including the structural arrangement of an opening defined on a tissue anchor that is sized and configured to receive a portion of the tissue anchor driver and/or material that forms a tissue anchor. Examples of tissue anchor drivers considered suitable to include in a kit include handheld, or mechanically driven, drivers, such as star (torx) drivers, slotted drivers, phillips head driver, allen wrench drivers, Robertson drivers, hex drivers, and any other driver considered suitable for a particular embodiment. Optionally, a kit can include a driver that is pre-loaded with a tissue anchor (e.g., a portion of the driver is disposed within a lumen defined by the screw and/or a suture is disposed through one, or both, of the passageways defined by a stem and/or the lumen of the screw). Examples of drill bits considered suitable to include in a kit include handheld, or mechanically driven drill bits, drill bits that have an outside diameter at the distal end equal to, greater than, less than, or about 0.236 inches, and any other drill bit considered suitable for a particular embodiment. Examples of reamers considered suitable to include in a kit include handheld, or mechanically driven reamers, reamers that have an outside diameter along the blade equal to, greater than, less than, or about 0.236 inches, reamers that have a blade length equal to, greater than, less than, or about 0.386 inches, reamers that include a bore through a portion, or the entirety, its length, and any other reamer considered suitable for a particular embodiment. Examples of beath pins considered suitable to include in a kit include beath pins that have an outside diameter equal to, greater than, less than, or about 2.44 millimeters, and any other beath pin considered suitable for a particular embodiment. Examples of materials considered suitable to form a tissue anchor driver, a reamer, and/or a beath pin include biocompatible materials, materials that can be made biocompatible, metals such as stainless steel, titanium, metal alloys, thermoplastics, polymers, nylon, polyethylene, high-density polyethylene (HDPE), high-performance polyethylene (HPPE), polyurethane, silicone, combinations of the materials described herein, and any other material considered suitable for a particular embodiment.

A storage container included in a kit can have any suitable structural arrangement and be formed of any suitable material and selection of a suitable structural arrangement and material to form a storage container can be based on various considerations, including the number of tissue anchors included in a kit. Examples of structural arrangements considered suitable to form a storage container include boxes, boxes that include a lid, boxes that include a lid attached to the box (e.g., pivotably attached), bags, and any other structural arrangement considered suitable for a particular embodiment. Examples of materials considered suitable to form a storage container include woods, metals, plastics, cardboards, fabrics, and any other material considered suitable for a particular embodiment. In the illustrated embodiment, the storage container 224 is a box 240 formed of a plastic.

While each tissue anchor 202, 204, 206 has been illustrated as including a screw and a stem, a kit that includes one or more tissue anchors can include a plurality of screws and a single, or multiple stems. Each stem included in the kit can be sized and configured to be received by more than one screw such that the stem can be utilized with more than one screw and implanted into the body of a patient. For example, a kit can include a first screw, a second screw, and a third screw, or any other suitable number of screws, and a single stem, or any other suitable number of stems. Each stem included in the kit, or a portion of each stem, can be sized and configured to be received by one of the first screw, second screw, and/or third screw.

Optionally, various components described herein can included in separate kits. For example, a first kit can include a tissue anchor according to an embodiment, a tissue anchor driver, a suture, a reamer, and a storage container and a second, separate, kit can include a beath pin, a needle, a suture loop, a graft sizing block, and a storage container 220. Optionally, one, or both, of the two kits can include instructions for use.

Various methods of treatment are described herein. While the methods described herein are shown and described as a series of acts, it is to be understood and appreciated that the methods are not limited by the order of acts, as some acts may in accordance with these methods, occur in the order shown and described, in different orders, and/or concurrently with other acts described herein.

Figure 17:
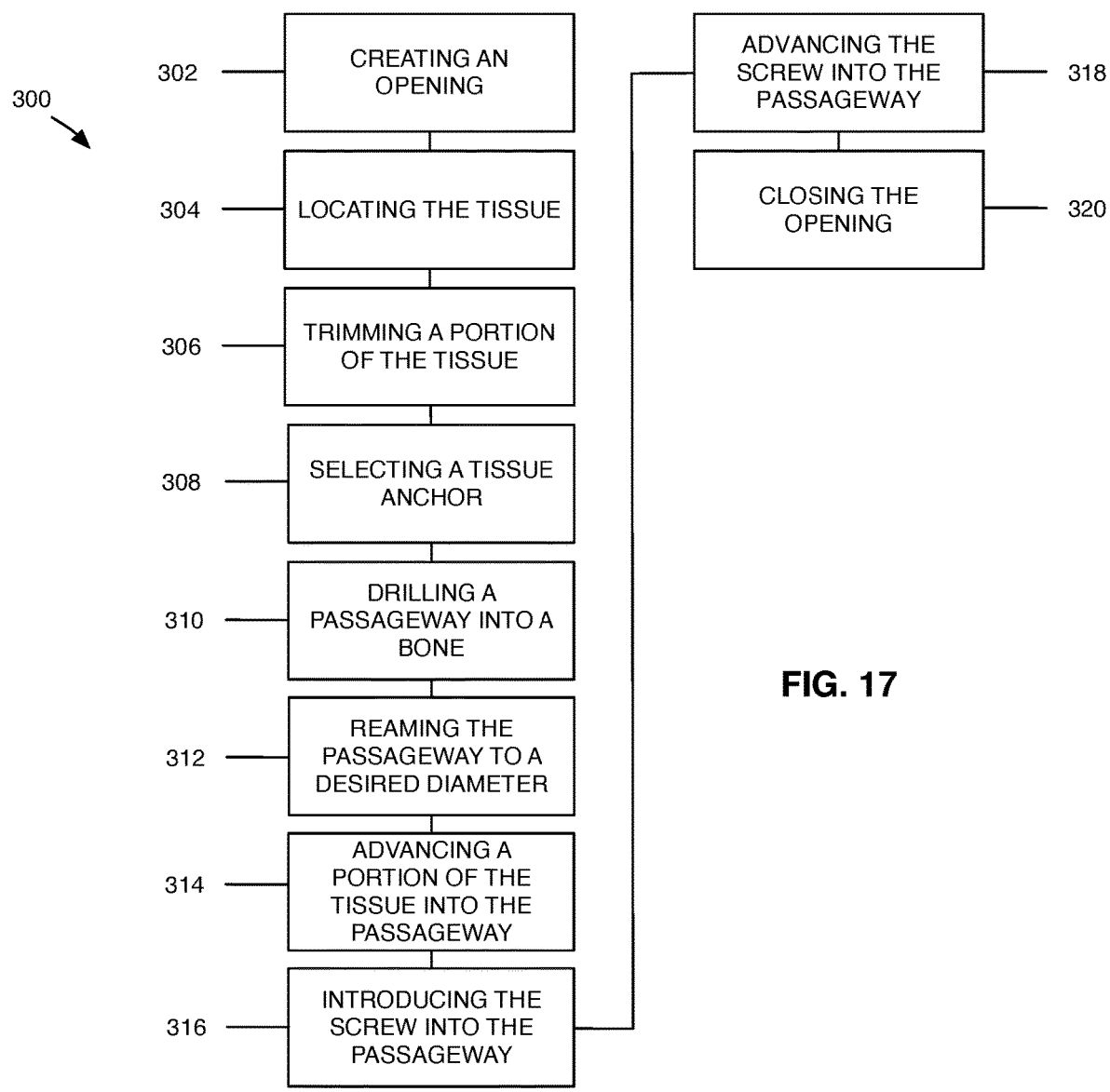
FIG. 17 is a schematic illustration of an example method of anchoring tissue to a bone.

FIG. 17 is a schematic illustration of a method 300 of anchoring tissue to a bone using an interference fit such that the tissue is anchored between the wall of the bone and a tissue anchor.

A step 302 comprises creating an opening over the tissue intended to be anchored to a bone. Another step 304 comprises locating the tissue. Another step 306 comprises trimming a portion of the tissue. Another step 308 comprises selecting a tissue anchor. Another step 310 comprises drilling a passageway into a bone. Another step 312 comprises reaming the passageway to a desired diameter based on the diameter of the selected tissue anchor. Another step 314 comprises advancing a portion of the tissue into the passageway such that a portion of the tissue is disposed within the passageway. Another step 316 comprises introducing the screw of the selected tissue anchor into the passageway containing a portion of the tissue such that a portion of the tissue disposed within the passageway is disposed adjacent to the distal portion of the screw. Another step 318 comprises advancing the screw into the passageway such that the tissue is anchored between the screw and the bone. Another step 320 comprises closing the opening.

Step 302 can be accomplished using any suitable medical device, such as a scalpel, or any other tool and can be performed using any suitable method and/or technique at any suitable location on a body. For example, in embodiments in which the tissue being treated is a bicep, step 302 can be accomplished using a scalpel to create an opening on, or near, the shoulder of a patient.

Step 304 can be accomplished using any suitable technique or method of visualizing the tissue intended to be anchored to a bone. Examples of suitable techniques and methods of visualizing tissue include using direct visualization, using a scope, and any other technique or method considered suitable for a particular embodiment. In embodiments, in which a scope is used, other steps that can be included in a method of anchoring tissue to a bone include applying a force on a scope toward the opening until a portion of the scope is disposed within the body of the patient and observing the body of the patient through the scope to identify the tissue intended to be anchored to a bone.

Step 306 can be accomplished using any suitable medical device, such as a scalpel or scissors, or any other tool and can be performed using any suitable method and/or technique. For example, in embodiments in which the tissue being treated is a bicep, step 306 can be accomplished using a scalpel to trim a portion of the bicep (e.g., near the end that has torn from the bone). Optionally, step 306 can be omitted from method 300 in embodiments in which the tissue being repaired does not require trimming.

Step 308 can be accomplished using any suitable tissue anchor and selection of a suitable tissue anchor can be based on various considerations, including the anatomy of the patient being treated. For example, step 308 can be accomplished by visualizing the tissue intended to be repaired and/or the bone to which the tissue is intended to be anchored to determine which type of tissue anchor should be selected. Examples of tissue anchors and/or screws considered suitable to use to complete method 300, or any other method described herein, include tissue anchor 10, tissue anchor 110, variations of the tissue anchors described herein, screw 712, screw 812, tissue anchors that include alternative screws, such as screw 712, and/or screw 812, and/or any other tissue anchor and/or screw considered suitable for a particular embodiment. In the illustrated embodiment, tissue anchor 10 has been used to illustrate performance of method 300, as shown in FIGS. 17A, 17B, 17C, and 17D.

Figure 17A:
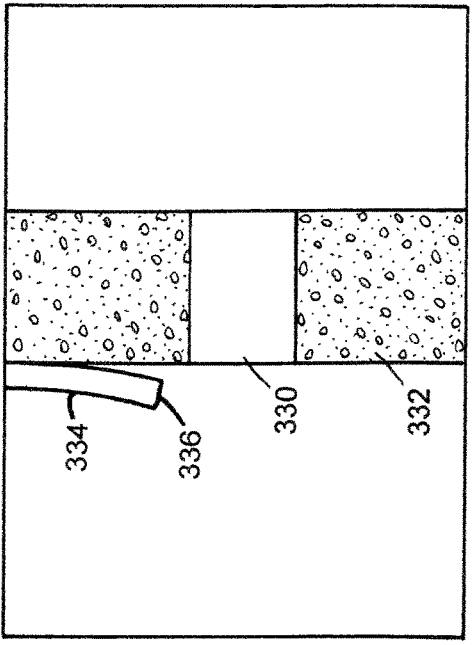
FIG. 17A illustrates a passageway intended to receive a tissue anchor and a portion of tissue separated from a bone.

Step 310 can be accomplished by drilling a passageway at a desired location on a bone. Step 310 can be accomplished using any suitable drill and a drill bit that has a first outside diameter. FIG. 17A illustrates a passageway 330 drilled into bone 332 and a portion of tissue 334 separated from the bone 332. The tissue 334 has an end 336 that has been trimmed, as described in step 306. A passageway can have any suitable diameter (e.g., sized and configured to allow a portion of, or the entirety of, a tissue anchor to pass into the passageway) and/or depth (e.g., greater than, less than, or equal to the length of the selected tissue anchor), and can have any suitable configuration. In the illustrated embodiment, the passageway 330 extends through the entire thickness of the bone 332. However, alternative embodiments can include a passageway that extends through only a portion of the thickness of a bone (e.g., creating a blind passageway). A drill bit used complete any step of the methods described herein can have any suitable outside diameter and selection of a suitable outside diameter for a drill bit can be based on various considerations, including the structural arrangement of a tissue anchor intended to be implanted in a bone.

A passageway can be drilled at any suitable location and on any suitable bone, or portion of the body, and selection of a suitable location to drill a passageway and a suitable bone, or portion of the body, to drill a passageway can be based on various considerations, including the treatment intended to be performed. Examples of suitable locations to drill a passageway include at, or near, an original point of attachment of the tissue on a calcaneus (e.g., Achilles tendon attachment), a tarsal, a tibia, a fibula, a scapula, a humerus, a tibia, a femur, a radius, and any other location considered suitable for a particular embodiment (e.g., posterior tibial tendon attachment, any other location where a tendon attaches to a portion of the foot or ankle). Examples of bones, or portions of the body, considered suitable to drill a passageway include the calcaneus, tarsal, talus, tibia, fibula, scapula, humerus, tibia, femur, radius, and any other bone, or portion of the body, considered suitable for a particular embodiment.

Step 312 can be accomplished using any suitable drill and a drill bit that has a second outside diameter that is greater than the first outside diameter (e.g., reamer). The diameter of the passageway created in the bone in step 312 is sized and configured to allow a portion of, or the entirety of, the selected tissue anchor to pass into the passageway. Optionally, step 312 can be omitted from method 300 in embodiments in which the passageway created in step 310 is sufficiently sized to receive a portion, or the entirety, of the selected tissue anchor.

Figure 17B:
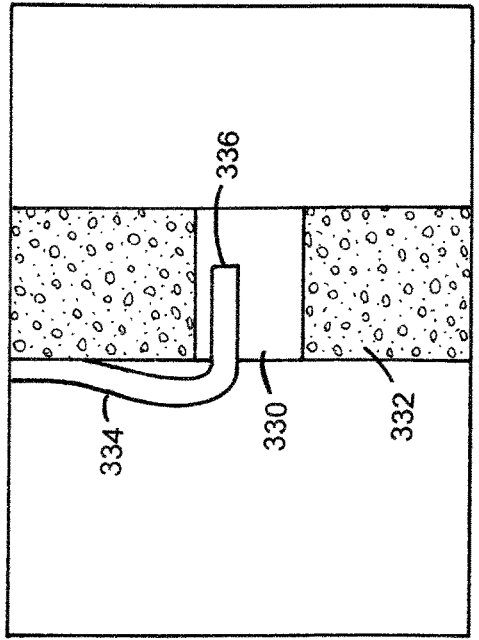
FIG. 17B illustrates a passageway intended to receive a tissue anchor and a portion of tissue separated from a bone. The tissue is partially disposed within the passageway.

Step 314 can be accomplished using any medical device (e.g., beath pin), such as forceps, or the hands of an individual, and until a desired portion of the tissue is disposed within the passageway. For example, step 314 can be accomplished by applying a force on a portion of the tissue directed toward the passageway such that a portion of the tissue is disposed within the passageway. FIG. 17B illustrates a portion of the length of the tissue 334 disposed within a passageway 330 that has been reamed such that the end 336 of the portion of the tissue 334 is disposed within the passageway 330. Alternative embodiments, however, can position a portion of tissue within a passageway that has not been reamed and/or such that the end of the tissue is disposed outside of the passageway (e.g., in embodiments in which the tissue is folded over on itself).

Figure 17C:
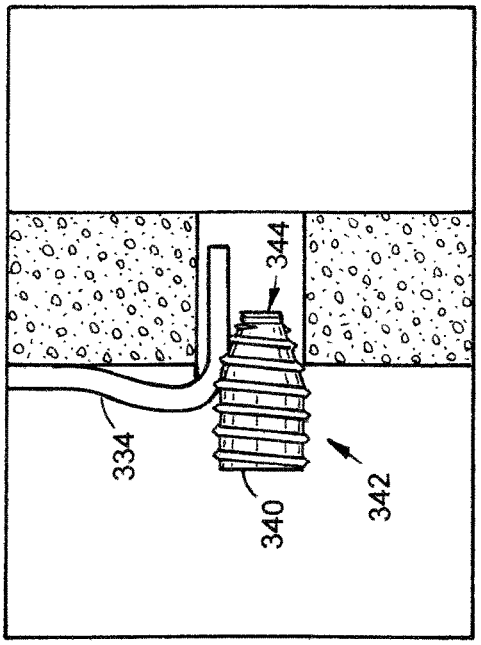
FIG. 17C illustrates a passageway, a tissue anchor partially disposed within the passageway, and a portion of tissue separated from a bone partially disposed within the passageway.

Step 316 can be accomplished using any medical device (e.g., driver), such as forceps, or the hands of an individual, and until the screw is partially disposed within the passageway and a portion of the tissue disposed within the passageway is disposed adjacent the distal portion of the screw. For example, step 316 can be accomplished by applying a force on the screw of the selected tissue anchor directed toward the passageway containing a portion of the tissue until a portion of the screw is disposed within the passageway. In embodiments in which the screw of the tissue anchor includes a distal portion that tapers from the proximal portion to the screw distal end, step 316 can be accomplished such that a portion of the tissue disposed within the passageway is disposed adjacent the tapered distal portion of the screw. FIG. 17C illustrates a tissue anchor 340 that has a screw 342 and a stem 344. The tissue anchor 340 is partially disposed within the passageway 330 and adjacent to a portion of the tissue 334.

Step 318 can be accomplished by introducing a tool into a first opening defined by a screw such that the distal end of the tool engages with the inner surface of the first opening and applying torque to any suitable portion of the tool such that the applied torque is transferred to the tissue anchor. Torque can be applied in the clockwise direction to rotatably advance the tissue anchor into the passageway (e.g., using a driver). An optional step comprises applying torque on any suitable portion of the tool in the counterclockwise direction to rotatably withdraw the tissue anchor from the passageway. Alternatively, in embodiments in which the thread of a screw extends in a counterclockwise direction, torque can be applied in the counterclockwise direction to rotatably advance the tissue anchor into the passageway and in a clockwise direction to rotatably withdraw the tissue anchor from the passageway.

Figure 17D:
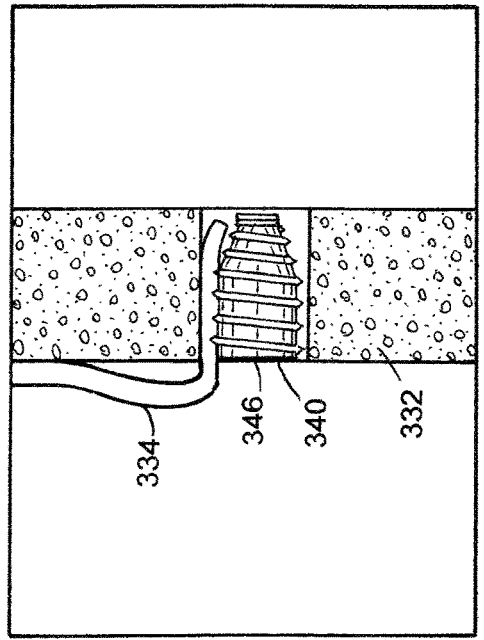
FIG. 17D illustrates a passageway, a tissue anchor disposed within the passageway, and a portion of tissue partially disposed within the passageway and anchored to the bone by the tissue anchor.

The torque applied to the tool is relative to the longitudinal axis of the tissue anchor and can be applied until the tissue anchor contacts the portion of the tissue disposed within the passageway, the tissue anchor compresses the tissue disposed within the passageway against the wall of the bone, and/or a predetermined, or desired, final position the tissue anchor and/or tissue being treated has been achieved. For example, torque can be applied on the tool until the tissue anchor is positioned within the passageway at a desired depth (e.g., such that a screw proximal end is near, adjacent, or coplanar with, the surface of the bone). FIG. 17D illustrates the tissue anchor 340 advanced into the passageway 330 such that it contacts a portion of the tissue 334 disposed within the passageway 330 and the tissue anchor proximal end 346 is coplanar with a surface of the bone 332. It is considered advantageous to utilize a tissue anchor that has a screw with a screw main body that tapers along a distal portion and includes a blunted crest at least because these tissue anchors decrease the potential for damaging the tissue during performance of the procedure.

While the tissue anchor 340 has been illustrated in FIG. 17D as being positioned such that the tissue anchor proximal end 346 is coplanar with a surface of the bone 332, a tissue anchor can be advanced into a bone such that a tissue anchor proximal end is positioned at any suitable location relative to a surface of a bone. Selection of a suitable position for a tissue anchor proximal end relative to a surface of a bone can be based on various considerations, including the treatment being performed. Examples of positions of tissue anchors considered suitable include those in which a tissue anchor proximal end is positioned above a surface of the bone (e.g., such that the tissue anchor protrudes from the bone), coplanar with a surface of the bone, within a passageway defined within the bone (e.g., the tissue anchor is countersunk), and any other position considered suitable for a particular embodiment.

Step 320 can be accomplished using any suitable device and/or method, such as by suturing the opening created in step 302 using a suture and needle.

While method 300 has been described as anchoring tissue to a bone, a tissue anchor, such as those described herein, can be used to anchor tissue to any suitable device, feature, element, component, or portion of a body. Selection of a suitable device, feature, element, component, or portion of a body to anchor tissue using a tissue anchor can be based on various considerations, including the material that forms the tissue intended to be anchored. Examples of devices, features, elements, components, and portions of a body considered suitable to anchor tissue using a tissue anchor, such as those described herein, include bone, other tissue, plates, and any other device, feature, element, component, and/or portion of a body considered suitable for a particular embodiment.

Figure 18:
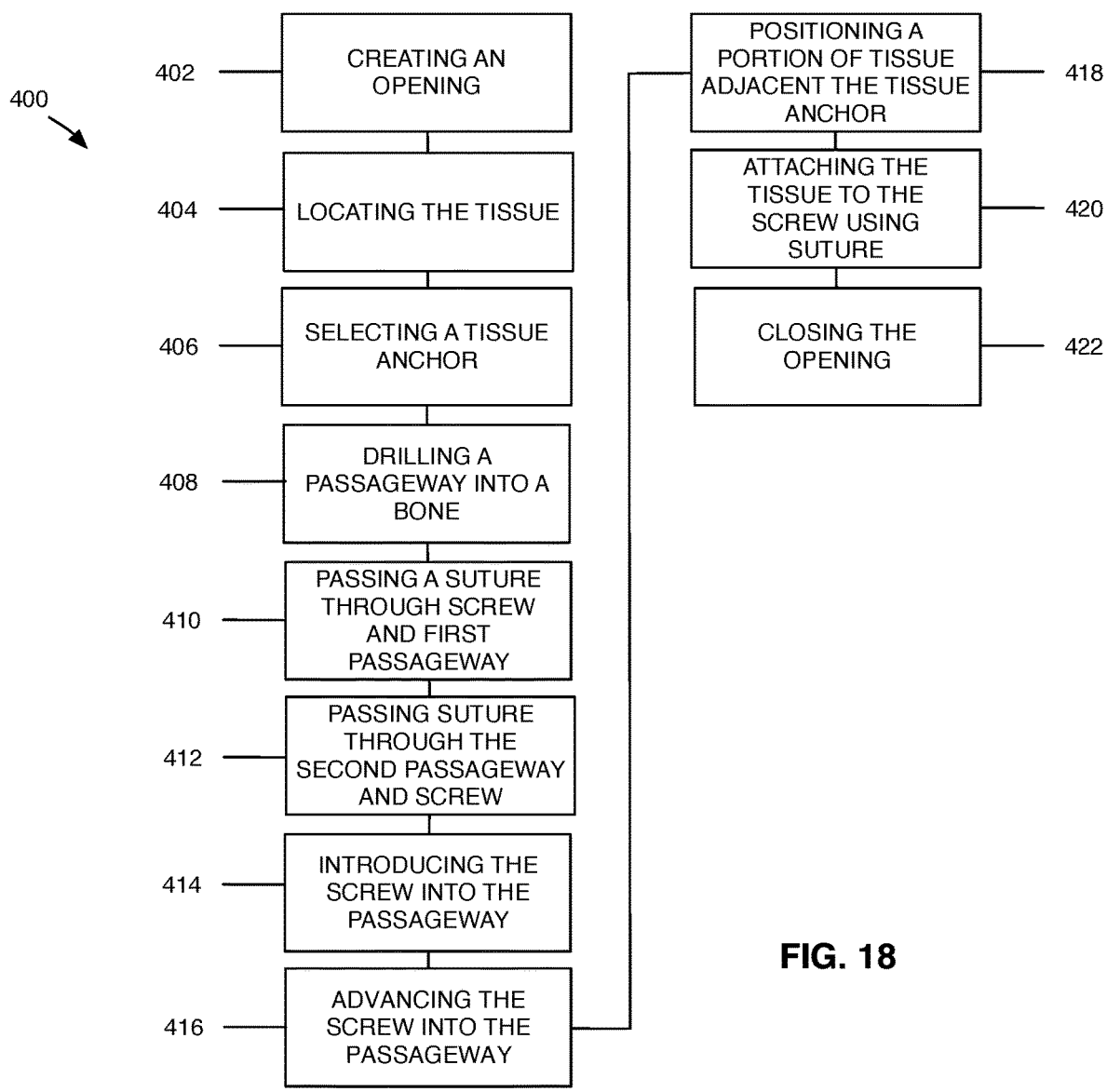
FIG. 18 is a schematic illustration of another example method of anchoring tissue to a bone.

FIG. 18 is a schematic illustration of a method 400 of anchoring tissue to a bone using a suture anchor.

A step 402 comprises creating an opening over the tissue intended to be anchored to a bone. Another step 404 comprises locating the tissue. Another step 406 comprises selecting a tissue anchor. Another step 408 comprises drilling a passageway into a bone. Another step 410 comprises passing the first end of a suture through the lumen defined by the screw and the first passageway defined by the stem. Another step 412 comprises passing the first end of the suture through the second passageway defined by the stem and through the lumen defined by the screw such that the first and second ends of the suture are disposed outside of the screw. Another step 414 comprises introducing the screw of the selected tissue anchor into the passageway such that a portion of the tissue anchor is disposed within the passageway. Another step 416 comprises advancing the screw into the passageway. Another step 418 comprises positioning a portion of the tissue adjacent the tissue anchor. Another step 420 comprises attaching the tissue to the screw using the suture such that the tissue is anchored to the screw. Another step 422 comprises closing the opening.

Step 402 can be accomplished as described above with respect to step 302. Step 404 can be accomplished as described above with respect to step 304. Step 406 can be accomplished as described above with respect to step 308. Step 408 can be accomplished as described above with respect to step 310.

Figure 18A:
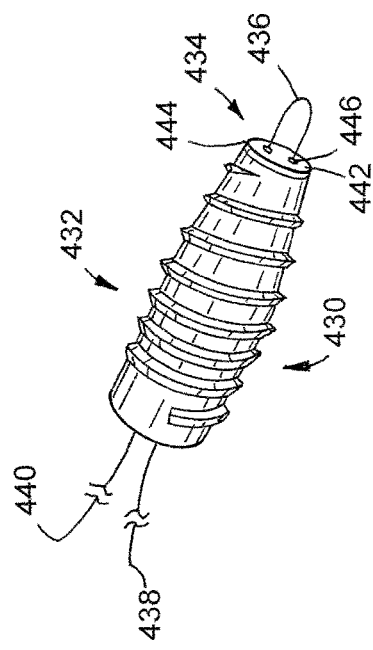
FIG. 18A illustrates a suture partially disposed through a tissue anchor. The suture is disposed through the lumen of the screw and the first passageway defined by the stem.

Step 410 can be accomplished using any suitable medical device, such as forceps, a guide wire, or the hands of an individual and a suture having any suitable structural arrangement and formed of any suitable material. For example, step 410 can be accomplished by applying a first force on a suture that is directed toward the tissue anchor such that the first end of the suture is passed through the lumen defined by the screw and the first passageway defined by the stem. FIG. 18A illustrates a tissue anchor 430 that has a screw 432 and a stem 434 and a suture 436 that has a first end 438 and a second end 440. The stem 434 is releasable attached to the screw 432. The stem main body 442 defines a first passageway 444 and a second passageway 446. The first end 432 of the suture 430 has been passed through the lumen defined by the screw 432 and the first passageway 444 defined by the stem 434.

Figure 18B:
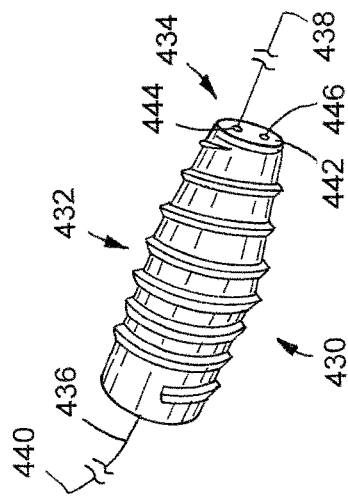
FIG. 18B illustrates a suture partially disposed through a tissue anchor. The suture is disposed through the lumen of the screw, the first passageway defined by the stem, and the second passageway defined by the stem.

Step 412 can be accomplished using any suitable medical device, such as forceps, a guide wire, or the hands of an individual. For example, step 412 can be accomplished by applying a second force on a suture that is directed toward the tissue anchor such that the first end of the suture is passed through the second passageway defined by the stem and through the lumen defined by the screw and the first and second ends of the suture are disposed outside of the screw. FIG. 18B illustrates the suture 436 passed through the lumen defined by the screw 432 and through each of the first and second passageways 444, 446 defined by the stem 434. Step 410 and step 412 can be accomplished prior to, or subsequent to, step 402, step 404, step 406, step 408, step 414, step 416, and/or step 418. Alternatively, in embodiments in which an open passageway is created through the thickness of the bone, step 410 and/or step 412 can be accomplished prior to, or subsequent to, step 402, step 404, step 406, step 408, step 414, step 416, and/or step 418 and through the open passageway.

Step 414 can be accomplished as described above with respect to step 316. Step 416 can be accomplished as described above with respect to step 318.

Figure 18C:
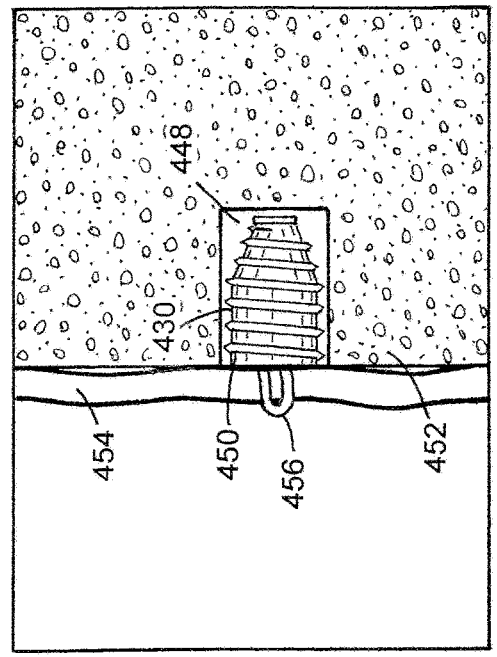
FIG. 18C illustrates a passageway, a tissue anchor disposed within the passageway, and a portion of tissue separated from a bone disposed adjacent to the tissue anchor.

Step 418 can be accomplished using any medical device, such as forceps, or the hands of an individual, and until the tissue is positioned adjacent a portion of the tissue anchor (e.g., screw proximal end). For example, step 418 can be accomplished by applying a force on a portion of the tissue directed toward the tissue anchor such that a portion of the tissue is disposed adjacent the tissue anchor. FIG. 18C illustrates the tissue anchor 430 advanced into the passageway 448 such that the tissue anchor proximal end 450 is coplanar with a surface of the bone 452 and a portion of the tissue 454 is disposed adjacent to the tissue anchor 430.

Figure 18D:
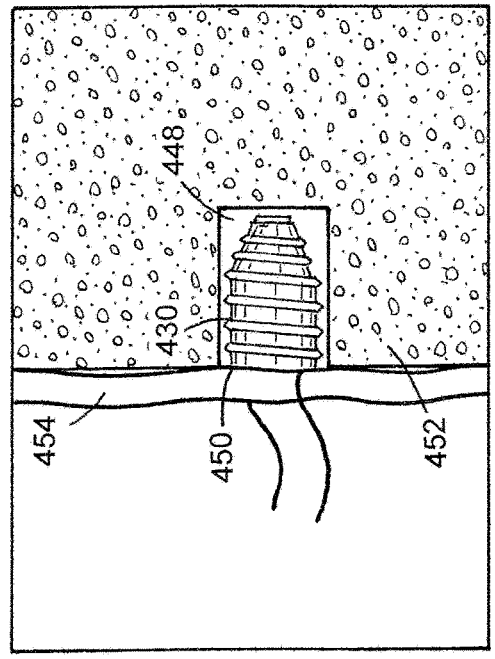
FIG. 18D illustrates a passageway, a tissue anchor disposed within the passageway, and a portion of tissue attached to the tissue anchor.

Step 420 can be accomplished using any medical device, such as forceps, or the hands of an individual, and by using any suitable technique or method of attachment between tissue and a suture. Selection of a suitable technique or method of attachment between tissue and a suture can be based on various considerations, including the material that forms the suture. Examples of techniques and methods of attachment considered suitable between tissue and a suture include tying a knot, or multiple knots, passing the suture through one or more portions of the tissue, combinations of the techniques and methods described herein, and any other technique or method considered suitable for a particular embodiment. FIG. 18D illustrates the portion of the tissue 454 attached to the tissue anchor 430 using a knot 456.

Step 422 can be accomplished as described above with respect to step 320.

Figure 19:
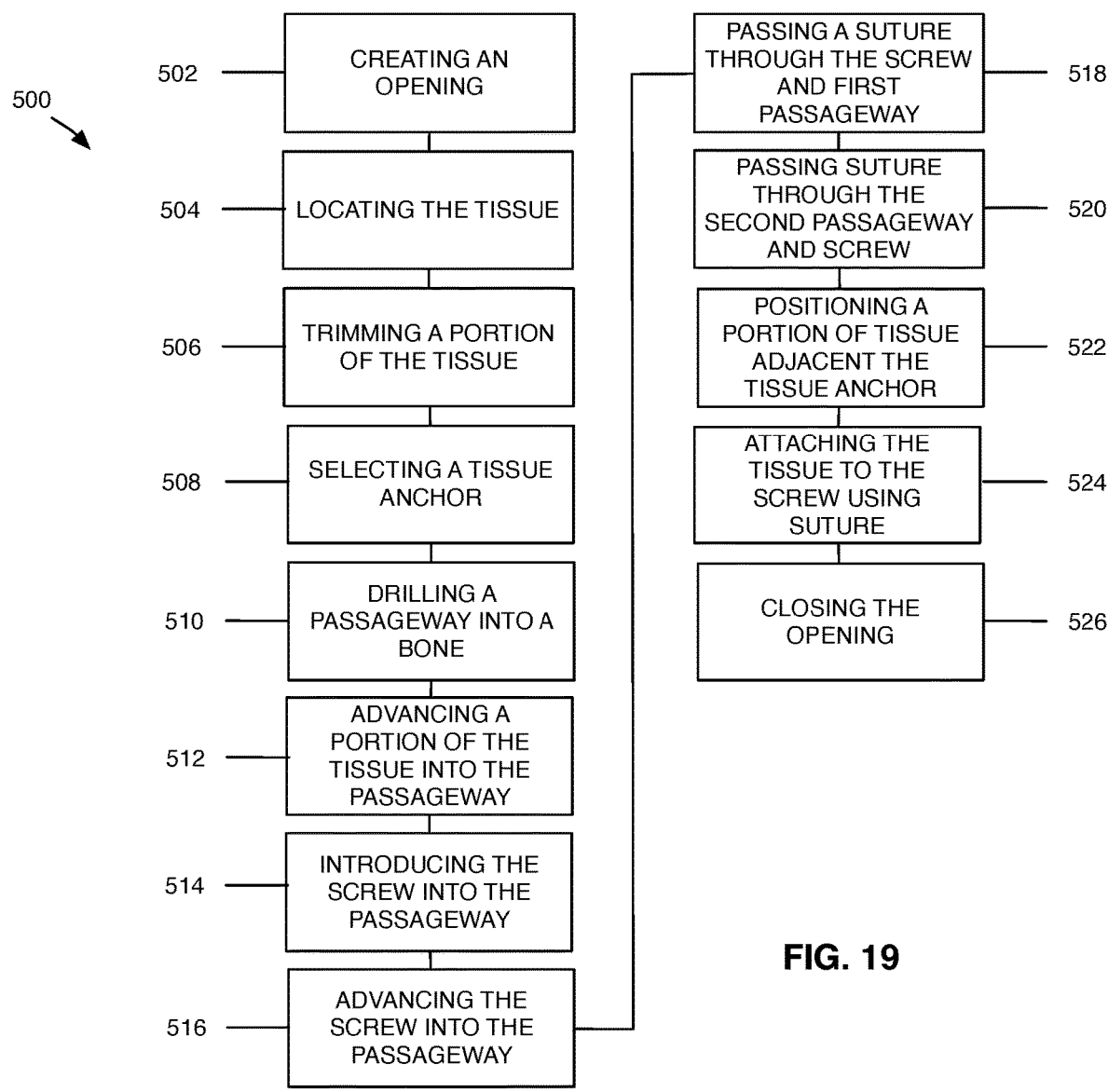
FIG. 19 is a schematic illustration of another example method of anchoring tissue to a bone.

FIG. 19 is a schematic illustration of a method 500 of anchoring tissue to a bone using an interference fit and a suture anchor.

A step 502 comprises creating an opening over the tissue intended to be anchored to a bone. Another step 504 comprises locating the tissue. Another step 506 comprises trimming a portion of the tissue. Another step 508 comprises selecting a tissue anchor. Another step 510 comprises drilling a passageway into a bone. Another step 512 comprises advancing a portion of the tissue into the passageway such that a portion of the tissue is disposed within the passageway. Another step 514 comprises introducing the screw of the selected tissue anchor into the passageway such that a portion of the tissue anchor is disposed within the passageway. Another step 516 comprises advancing the screw into the passageway such that the tissue is anchored between the screw and the bone. Another step 518 comprises passing the first end of a suture through the lumen defined by the screw and the first passageway defined by the stem. Another step 520 comprises passing the first end of the suture through the second passageway defined by the stem and through the lumen defined by the screw such that the first and second ends of the suture are disposed outside of the screw. Another step 522 comprises positioning a portion of the tissue adjacent the tissue anchor. Another step 524 comprises attaching the tissue to the screw using the suture such that the tissue is anchored to the screw. Another step 526 comprises closing the opening.

Step 502 can be accomplished as described above with respect to step 302. Step 504 can be accomplished as described above with respect to step 304. Step 506 can be accomplished as described above with respect to step 306. Step 508 can be accomplished as described above with respect to step 308.

Step 510 can be accomplished as described above with respect to step 310 and/or 408. As shown in FIGS. 19A, 19B, 19C, and 19D, a passageway 530 has been created through the entire thickness of the bone 532.

Figure 19B:
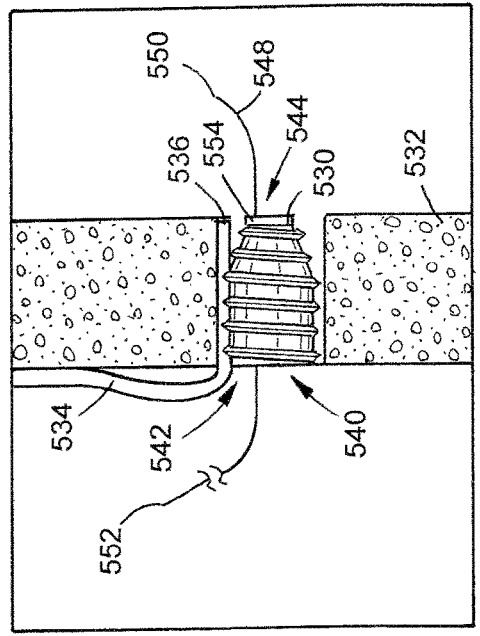
FIG. 19B illustrates a passageway, a portion of tissue separated from a bone partially disposed within the passageway, a tissue anchor disposed within the passageway, and a suture partially disposed through the tissue anchor. The suture is disposed through the lumen of the screw and the first passageway defined by the stem.
Figure 19D:
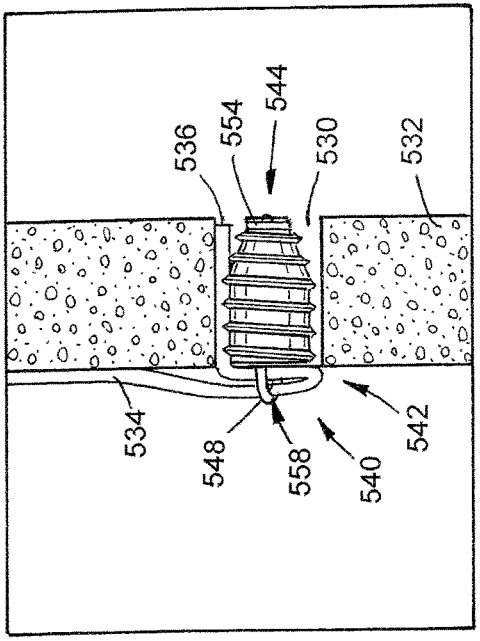
FIG. 19D illustrates a passageway, a tissue anchor disposed within the passageway, a portion of tissue partially disposed within the passageway and anchored to the bone by the tissue anchor, and a portion of tissue attached to the tissue anchor.
Figure 19A:
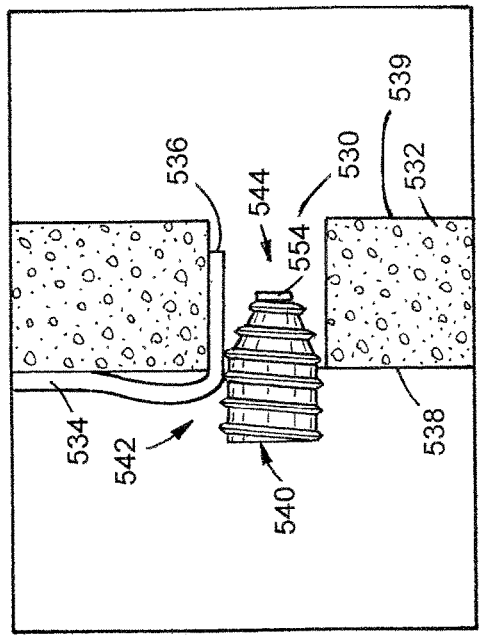
FIG. 19A illustrates a passageway, a portion of tissue separated from a bone partially disposed within the passageway, and a tissue anchor partially disposed within the passageway.

Step 512 can be accomplished as described above with respect to step 314. FIG. 19A illustrates a portion of the length of the tissue 534 disposed within the passageway 530 such that the end 536 of the portion of the tissue 534 is disposed within the passageway 530. Alternative embodiments, however, can position a portion of tissue within a passageway such that the end of the tissue is disposed outside of the passageway (e.g., on a first side 538 of the bone 530, or on a second side 539 of the bone 530).

Step 514 can be accomplished as described above with respect to step 316. FIG. 19A illustrates a tissue anchor 540 that has a screw 542 and a stem 544, The tissue anchor 540 is partially disposed within the passageway 530 and adjacent to the portion of the tissue 534 disposed within the passageway 530.

Step 516 can be accomplished as described above with respect to step 318. Step 518 can be accomplished as described above with respect to step 410. FIG. 19B illustrates the tissue anchor 540 advanced into the passageway 530 such that the tissue anchor proximal end is coplanar with a surface of the bone 532. In addition, FIG. 19B illustrates a suture 548 that has a first end 550 and a second end 552. The stem main body 554 defines a first passageway and a second passageway. The first end 550 of the suture 548 has been passed through the lumen defined by the screw 542 and the first passageway defined by the stem 544.

Figure 19C:
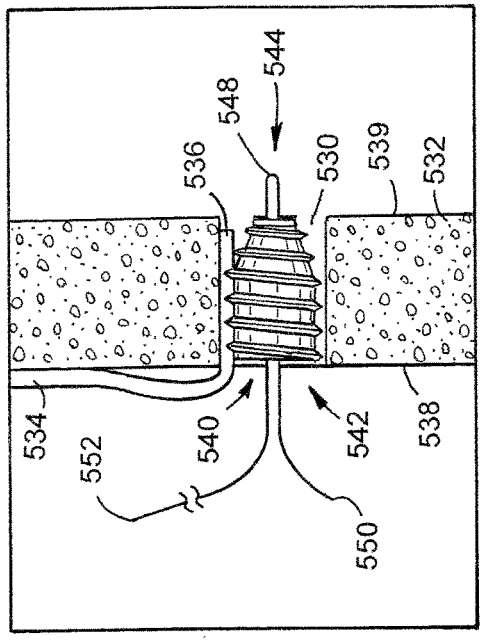
FIG. 19C illustrates a passageway, a portion of tissue separated from a bone partially disposed within the passageway, a tissue anchor disposed within the passageway, and a suture partially disposed through the tissue anchor. The suture is disposed through the lumen of the screw, the first passageway defined by the stem, and the second passageway defined by the stem.

Step 520 can be accomplished as described above with respect to step 412. FIG. 19C illustrates the suture 548 passed through the lumen defined by the screw 542 and through each of the first and second passageways defined by the stem 544.

Step 522 can be accomplished as described above with respect to step 418. FIG. 19D illustrates a portion of tissue 534 that is separated from the bone 532 disposed adjacent to the tissue anchor 530 (e.g., the proximal end of the screw 542).

Step 524 can be accomplished as described above with respect to step 420. FIG. 19D illustrates the portion of the tissue 534 attached to the tissue anchor 530 using a knot 558.

Step 526 can be accomplished as described above with respect to step 320.

Figure 20:
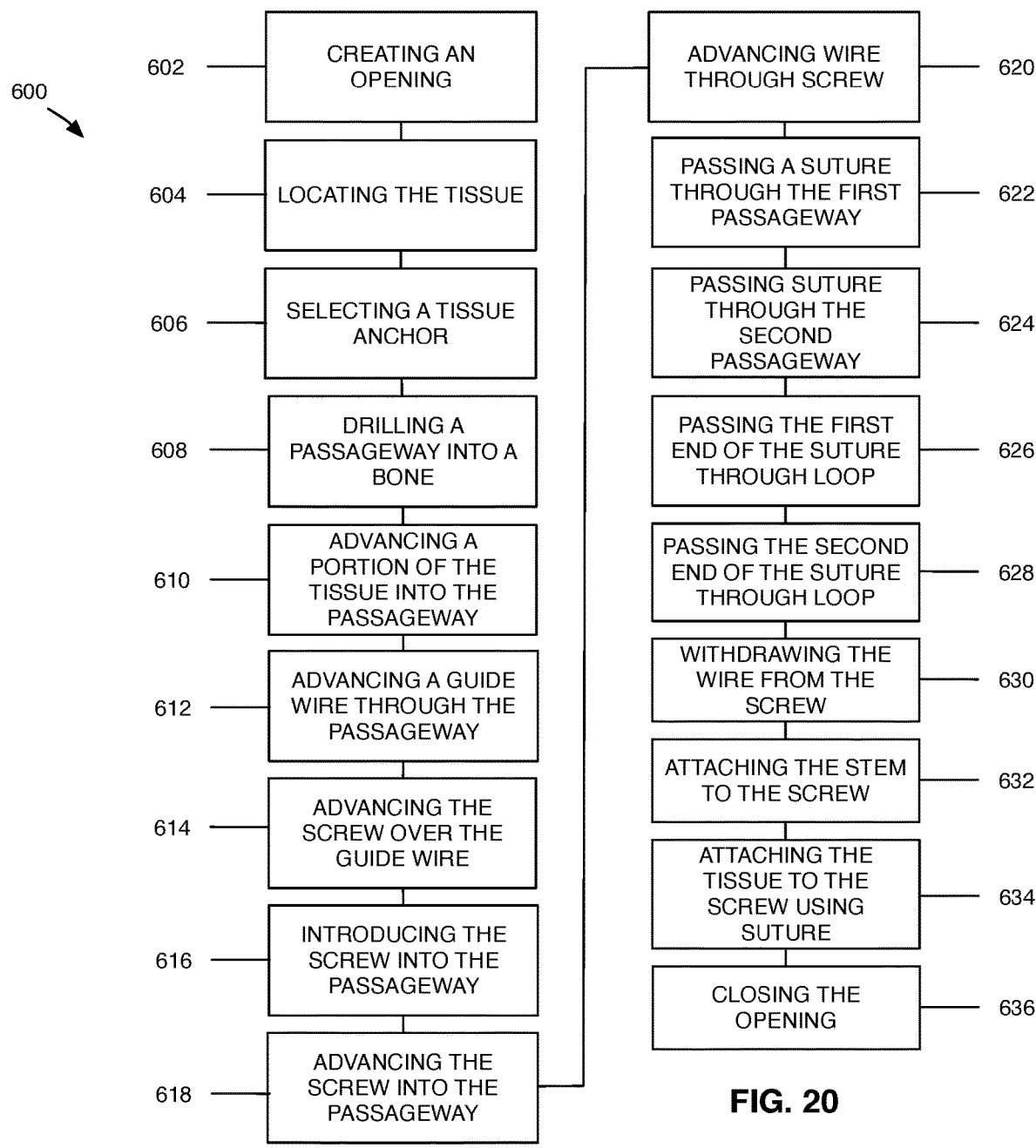
FIG. 20 is a schematic illustration of another example method of anchoring tissue to a bone.

FIG. 20 is a schematic illustration of another method 600 of anchoring tissue to a bone using an interference fit and a suture anchor.

A step 602 comprises creating an opening over the tissue intended to be anchored to a bone. Another step 604 comprises locating the tissue. Another step 606 comprises selecting a tissue anchor. Another step 608 comprises drilling a passageway into a bone. Another step 610 comprises advancing a portion of the tissue into the passageway such that a portion of the tissue is disposed within the passageway. Another step 612 comprises advancing a guide wire through the passageway such that a portion of the guide wire is disposed within the passageway. Another step 614 comprises advancing the screw of the selected tissue anchor over the guide wire such that the screw is disposed on the guide wire. Another step 616 comprises introducing the screw of the selected tissue anchor into the passageway such that a portion of the tissue anchor is disposed within the passageway. Another step 618 comprises advancing the screw into the passageway such that the tissue is anchored between the screw and the bone. Another step 620 comprises advancing a wire that has a first end, a second end, and that defines a loop on its second end through the lumen of the screw such that the first end of the wire is disposed on a first side of the screw and the second end of the wire is disposed on a second side of the screw. Another step 622 comprises passing the first end of a suture through the first passageway defined by the stem. Another step 624 comprises passing the first end of the suture through the second passageway defined by the stem. Another step 626 comprises passing the first end of the suture through the loop defined by the wire. Another step 628 comprises passing the second end of the suture through the loop defined by the wire. Another step 630 comprises withdrawing the wire and the portion of the suture disposed through the loop defined by the wire through the lumen defined by the screw such that the first and second ends of the suture are disposed outside of the screw. Another step 632 comprises attaching the stem to the screw. Another step 634 comprises attaching the tissue to the screw using the suture such that the tissue is anchored to the screw. Another step 636 comprises closing the opening.

Step 602 can be accomplished as described above with respect to step 302. Step 604 can be accomplished as described above with respect to step 304. Step 606 can be accomplished as described above with respect to step 308. Step 608 can be accomplished as described above with respect to step 310. As shown in FIGS. 20A, 20B, 20C, 20D, 20E, 20F, and 20G a passageway 640 has been created through the entire thickness of the bone 642.

Figure 20A:
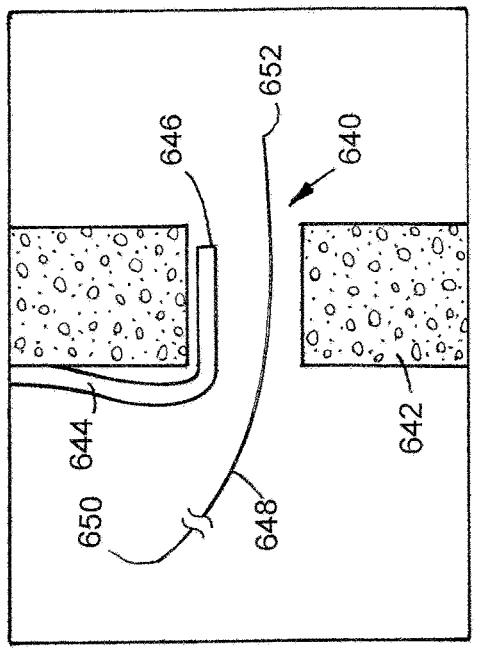
FIG. 20A illustrates a passageway and a portion of tissue separated from a bone partially disposed within the passageway.

Step 610 can be accomplished as described above with respect to step 314. FIG. 20A illustrates a portion of the length of the tissue 644 disposed within the passageway 640 such that the end 646 of the portion of the tissue 644 is disposed within the passageway 640.

Figure 20B:
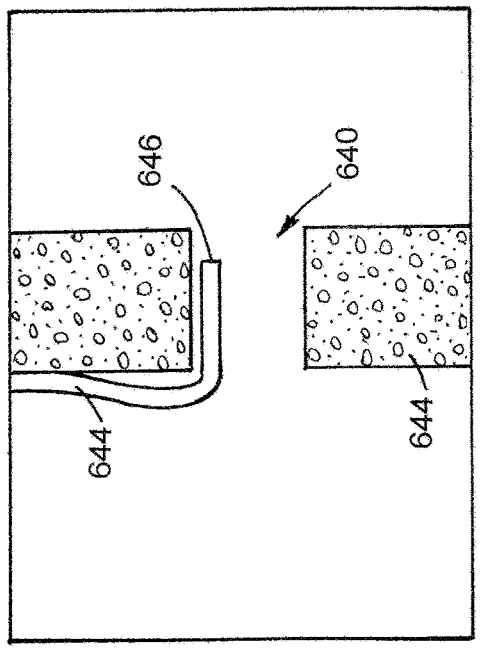
FIG. 20B illustrates a passageway, a portion of tissue separated from a bone partially disposed within the passageway, and a guide wire partially disposed within the passageway.

Step 612 can be accomplished using any suitable guide wire having any suitable length and diameter and selection of a suitable guide wire can be based on various considerations, including the diameter of the passageway created through a bone. Step 612 can be accomplished using any suitable medical device (e.g., beath pin), such as forceps, or the hands of an individual, and until the guide wire is disposed through the passageway, or partially disposed within the passageway, and a portion of the tissue disposed within the passageway is disposed adjacent the guide wire. For example, step 612 can be accomplished by applying a force on the guide wire directed toward the passageway containing a portion of the tissue until the guide wire is advanced through the passageway. FIG. 20B illustrates a guide wire 648 that has a first end 650 and a second end 652. As shown in FIG. 20B, the guide wire 648 has been advanced through the passageway 640.

Figure 20C:
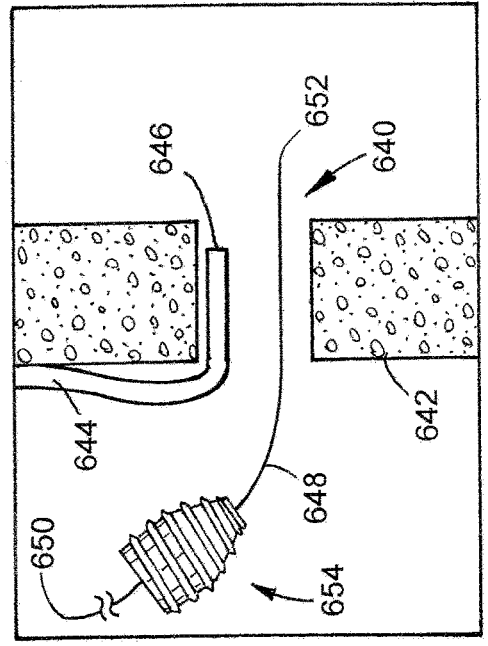
FIG. 20C illustrates a passageway, a portion of tissue separated from a bone partially disposed within the passageway, a guide wire partially disposed within the passageway, and a screw of a tissue anchor disposed on the guide wire.

Step 614 can be accomplished using any medical device, such as forceps, or the hands of an individual, and until the guide wire is passed through the lumen defined by the screw and the screw is disposed over the guide wire. For example, step 614 can be accomplished by applying a force on the screw of the selected tissue anchor directed toward the guide wire until the first end of the guide wire is passed through the lumen defined by the screw. FIG. 20C illustrates a screw 654 advanced over the guide wire 648 such that the guide wire 648 is disposed within the lumen defined by the screw 654.

Step 616 can be accomplished as described above with respect to step 316. An optional step comprises withdrawing the guide wire from the screw such that the guide wire is free of the screw and can be accomplished prior to, or subsequent to, step 616 or step 618. This optional step can be accomplished by applying a force on the guide wire away from the screw such that the guide wire is withdrawn from the lumen defined by the screw.

Figure 20E:
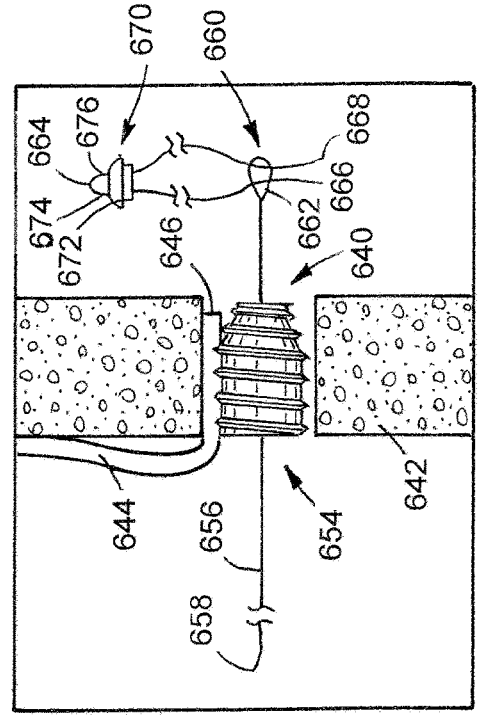
FIG. 20E illustrates a passageway, a portion of tissue separated from a bone partially disposed within the passageway, a screw of a tissue anchor disposed within the passageway, a wire partially disposed through the screw of the tissue anchor, and a suture partially disposed through the stem of the tissue anchor.
Figure 20G:
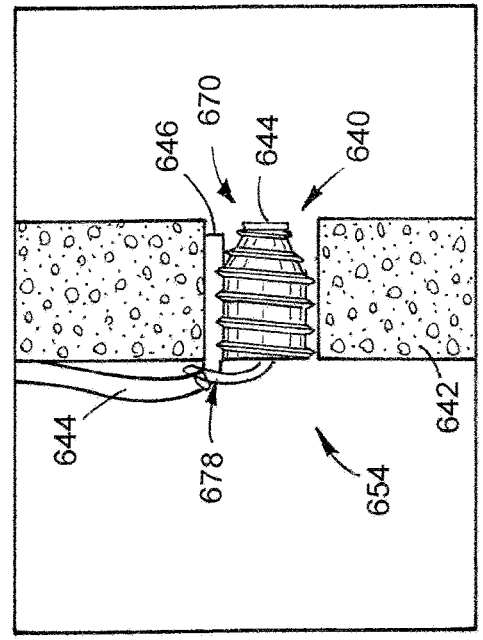
FIG. 20G illustrates a passageway, a tissue anchor disposed within the passageway, a portion of tissue partially disposed within the passageway and anchored to the bone by the tissue anchor, and a portion of tissue attached to the tissue anchor.
Figure 20D:
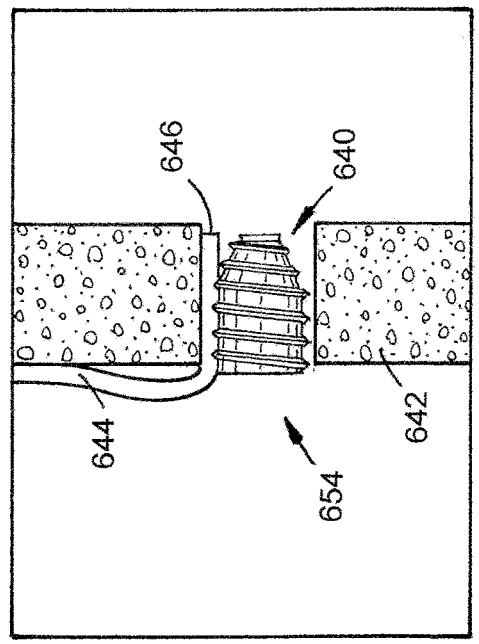
FIG. 20D illustrates a passageway, a portion of tissue separated from a bone partially disposed within the passageway, and a screw of a tissue anchor disposed within the passageway.

Step 618 can be accomplished as described above with respect to step 318. FIG. 20D illustrates the screw 654 advanced into the passageway 640 such that the screw proximal end is coplanar with a surface of the bone 642 and a portion of the tissue 644 is disposed adjacent to the screw 654.

Step 620 can be accomplished using any suitable wire (e.g., suture loop) having any suitable length, diameter, and defining a loop with any suitable diameter at its second end. Selection of a suitable wire can be based on various considerations, including the diameter of the passageway created through a bone. Step 620 can be accomplished using any suitable medical device, such as forceps, or the hands of an individual, and until the wire is disposed through the lumen defined by the screw. For example, step 620 can be accomplished by applying a force on the wire directed toward the lumen defined by the screw until the second end of the wire is advanced through the lumen defined by the screw. FIG. 20E illustrates a wire 656 that has a first end 658 and a second end 660 that defines a loop 662. As shown in FIG. 20E, the wire 656 has been advanced through the lumen defined by the screw 654.

Step 622 can be accomplished using any suitable medical device, such as forceps, a guide wire, or the hands of an individual and a suture having any suitable structural arrangement and formed of any suitable material. For example, step 622 can be accomplished by applying a first force on a suture that is directed toward the stem of a tissue anchor such that the first end of the suture is passed through the first passageway defined by the stem.

Step 624 can be accomplished using any suitable medical device, such as forceps, a guide wire, or the hands of an individual. For example, step 624 can be accomplished by applying a second force on a suture that is directed toward the stem of the tissue anchor such that the first end of the suture is passed through the second passageway defined by the stem and the first and second ends of the suture are disposed outside of the stem. FIG. 20E illustrates a suture 664 that has a first end 666 and a second end 668 and the stem 670. The stem 670 has a main body 672 defines a first passageway 674 and a second passageway 676. The first end 666 of the suture 664 has been passed through the first passageway 674 defined by the stem 670 and the second passageway 676 defined by the stem 670.

Step 626 can be accomplished using any suitable medical device, such as forceps, a guide wire, or the hands of an individual. For example, step 626 can be accomplished by applying a first force on the first end of the suture that is directed toward the loop defined by a wire until the first end of the suture is passed through the loop defined by the wire.

Step 628 can be accomplished using any suitable medical device, such as forceps, a guide wire, or the hands of an individual. For example, step 628 can be accomplished by applying a second force on the second end of the suture that is directed toward the loop defined by a wire until the second end of the suture is passed through the loop defined by the wire. FIG. 20E illustrates both the first end 666 and the second end 668 of the suture 664 disposed through the loop 662 defined by the wire 656.

Figure 20F:
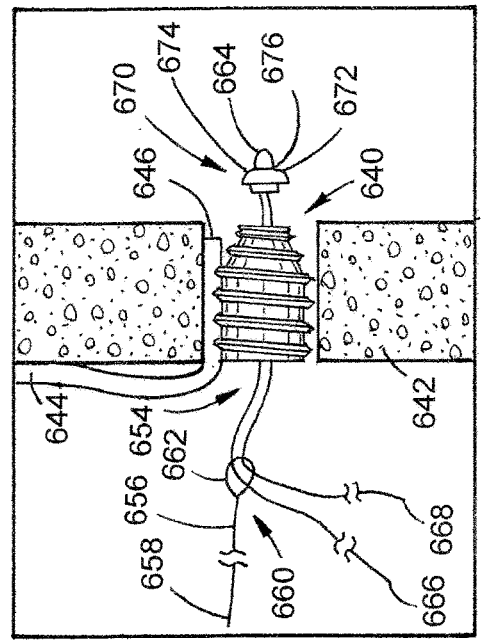
FIG. 20F illustrates a passageway, a portion of tissue separated from a bone partially disposed within the passageway, a screw of a tissue anchor disposed within the passageway, and a suture partially disposed through the stem of the tissue anchor, the screw of the tissue anchor, and a loop defined by the wire.

Step 630 can be accomplished using any suitable medical device, such as forceps, or the hands of an individual, and until the wire is withdrawn from the screw of the tissue anchor. For example, step 630 can be accomplished by applying a force on the wire directed away from the screw until the wire is withdrawn from the lumen defined by the screw and the first and second ends 666, 668 of the suture are advanced through the lumen defined by the screw. FIG. 20F illustrates the wire 656 withdrawn from the lumen defined by the screw 654.

Step 632 can be accomplished using any suitable medical device, such as forceps, or the hands of an individual, and until the stem is attached to the screw. For example, step 632 can be accomplished by applying a force on the suture directed away from the screw until the stem is attached to the screw using an interference fit between the screw and the stem. FIG. 20G illustrates the stem 670 attached to the screw 654.

Step 634 can be accomplished as described above with respect to step 420. FIG. 20G illustrates the portion of the tissue 644 attached to the tissue anchor using a knot 678.

Step 636 can be accomplished as described above with respect to step 320.

An alternative step that can be included in a method of anchoring tissue comprises the step of determining whether the tissue will be anchored to a bone using an interference fit, using a suture anchor, or both. This step can be completed prior to, concurrently with, or subsequent to, a step of creating an opening over the tissue intended to be anchored to a bone, a step of locating the tissue, a step of trimming a portion of the tissue, a step of drilling a passageway into a bone, and/or a step of reaming the passageway to a desired diameter. This step can be accomplished using any suitable technique or method of determining whether the tissue should be anchored to a bone using an interference fit, a suture anchor, or both, and selection of a suitable technique or method can be based on various considerations, including the anatomy of the patient being treated. For example, this step can be accomplished by visualizing the tissue intended to be attached to a bone and/or the bone to which the tissue is intended to be anchored to determine which type of attachment should be utilized.

It is considered advantageous to utilize a tissue anchor that is capable of being utilized as both an interference screw and as a suture anchor at least because such a tissue anchor provides a user with the ability to attach tissue to a bone using one or more methods using the same device. This is particularly advantageous in situations in which knowledge of the type of anchoring device that should be used is unknown until a surgical procedure has been initiated, allowing a user to select the appropriate anchoring device once a review of the tissue intended to be anchored and/or the bone have been inspected.

FIGS. 21, 22, 23, 24, and 25 illustrate an alternative screw 712 that can be included in a tissue anchor. The screw 712 is similar to the screw 12 illustrated in FIGS. 1, 2, 3, and 4 and described above, except as detailed below. The screw 712 has a lengthwise axis 719, a screw main body 720, and a thread 722. The screw main body 720 has a screw length 721, a screw proximal end 724, a first outside diameter 725, a screw distal end 726, a second outside diameter 727, and defines a first opening 728, a second opening 730, a lumen 732, a wall 734, a proximal portion 735, and a distal portion 737. The screw length 721 extends from the screw proximal end 724 to the screw distal end 726. The proximal portion 735 extends from the screw proximal end 724 toward the screw distal end 726. The distal portion 737 extends from the screw distal end 726 toward the screw proximal end 724. In the illustrated embodiment, the distal portion 737 extends from the proximal portion 735 to the screw distal end 726. In the illustrated embodiment, the outside diameter of the screw main body 720 tapers along the distal portion 737 of the screw main body 720.

The first outside diameter 725 is disposed at the screw proximal end 724 and the second outside diameter 727 is disposed at the screw distal end 726. The first opening 728 is defined at the screw proximal end 724 and the second opening 730 is defined at the screw distal end 726. Each of the first opening 728 and the second opening 730 is sized and configured to receive a portion of a hex drive to accomplish advancement of the screw into a portion of a body (e.g., bone). The second opening 730 is sized and configured to receive a portion of a stem. The lumen 732 extends from the first opening 728 to the second opening 730 and is sized and configured to receive one or more portions (e.g., lengths) of a suture and has a constant diameter, and cross-sectional configuration, along its length. Alternative embodiments, however, can include a lumen that has a cross-sectional configuration that varies along the length of the lumen. The wall 734 extends from the screw proximal end 724 to the screw distal end 726 and has a thickness along the screw length 721 such that no openings extend through the wall 734 and provide access to the lumen 732.

The thread 722 has a plurality of turns 738, a thread proximal end 740, a thread distal end 742, a thread length 743, a pitch 744, a height 746, a first side 748, a second side 750, a thickness 752, a root 754, a crest 756, a first portion 758, and a second portion 760. The thread length 743 extends from the thread proximal end 740 to the thread distal end 742 and is less than the screw length 721. The first portion 758 extends from the thread proximal end 740 toward the thread distal end 742 and the second portion 760 extends from the first portion 758 to the thread distal end 742. The height 746 of the thread 722 extends from the root 754 to the crest 756 and is constant along the first portion 758 of the of the thread 722 and tapers from the first portion 758 along the second portion 760 of the thread 722 to the thread distal end 742. The thickness 752 of the thread 722 extends from the first side 748 of the thread 722 to the second side 750 of the thread 722 at the root 754. The thickness 752 increases from the first portion 758 along the second portion 760 of the thread 722 to the thread distal end 742. In the illustrated embodiment, the crest 756 is blunted along the first portion 758 of the thread 722 and the second portion 760 of the thread 722. The inclusion of a crest 756 that is blunted along the length of the thread 722 is considered advantageous at least because it reduces the possibility of damaging tissue as the thread 722 is advanced into a passageway and the tissue is secured between the thread 722 and the wall defining the passageway (e.g., the wall defining a passageway created in a bone). This can be important because inclusion of a crest that is blunted can prevent tissue damage, including severing of the tissue, which could eliminate any anchoring provided by the tissue anchor.

In the illustrated embodiment, the screw length 721 is equal to about 0.591 inches, the thread height 746 is equal to about 0.028 inches, each thread includes a radius of curvature 770 equal to about 0.012 proximal, and adjacent, to the crest 756 and distal, and adjacent, to the crest 756, each thread includes a radius of curvature 772 equal to about 0.018 inches proximal, and adjacent, to the root 754 and distal, and adjacent, to the root 754, the lumen 732 has a hexagonal cross-sectional configuration and an inside diameter equal to about 0.1 inches, the pitch 744 is equal to about 0.079 inches, the thread has a thread angle 774 equal to about 48 degrees, a distal portion of the thread 722 (e.g., the thread second side 750) is disposed at an angle 776 equal to about 40 degrees relative to an axis that is disposed orthogonally to the lengthwise axis 719 of the screw 712, a proximal portion of the thread 722 (e.g., the thread first side 748) is disposed at an angle 778 equal to about 8 degrees relative to an axis that is disposed orthogonally to the lengthwise axis 719 of the screw 712, and the thread 722 has a major diameter 780 and a minor diameter 782. While particular dimensions have been described, a screw can have any suitable dimensions and selection of suitable dimensions can be based on various considerations, including the type of bone within which a screw is intended to be disposed. Example screw lengths considered suitable for a screw include those that are equal to, greater than, less than, or about 0.591 inches, those between about 0.4 inches and about 0.8 inches, and any other length considered suitable for a particular embodiment. Example thread heights considered suitable for a screw include those that are equal to, greater than, less than, or about 0.028 inches, those between about 0.02 inches and about 0.04 inches, and any other height considered suitable for a particular embodiment.

Example radii of curvature considered suitable for inclusion on a thread include those that are equal to, greater than, less than, or about 0.012 inches, 0.018 inches, those between about 0.005 inches and about 0.02 inches, those between about 0.01 inches and about 0.03 inches, and any other radius of curvature considered suitable for a particular embodiment. Example inside diameters considered suitable for lumen of a screw include those that are equal to, greater than, less than, or about 0.1 inches, those between about 0.05 inches and about 0.15 inches, and any other inside diameter considered suitable for a particular embodiment. Example pitches considered suitable for a thread include those that are equal to, greater than, less than, or about 0.079 inches, those between about 0.06 inches and about 0.1 inches, and any other pitch considered suitable for a particular embodiment. Example thread angles considered suitable for a screw include those that are equal to, greater than, less than, or about 48 degrees, those between about 38 degrees and about 58 degrees, and any other thread angle considered suitable for a particular embodiment. Example major diameters considered suitable for a screw include those that are equal to, greater than, less than, or about 0.225 inches, 0.227 inches, 0.229 inches, those between about 0.2 inches and about 0.3 inches, those less than 0.2 inches, those greater than 0.3 inches, and any other diameter considered suitable for a particular embodiment. Example minor diameters considered suitable for a screw include those that are equal to, greater than, less than, or about 0.169 inches, 0.171 inches, 0.173 inches, those between about 0.1 inches and about 0.2 inches, those less than 0.1 inches, those greater than 0.2 inches, and any other diameter considered suitable for a particular embodiment.

Any suitable technique or method of manufacture can be utilized to form a screw and selection of a suitable technique or method can be based on various considerations, such as the material that forms a screw. For example, a blank used to form a screw can include a radius of curvature equal to about 0.05 inches that extends from a proximal end of the blank to an outer surface of the blank and a distal end of the blank can include a radius of curvature equal to about 0.005 inches. In addition, a blank used to form a screw can include a distal portion that extends from a location between a proximal end of the blank and a distal end of the blank to the distal end of the blank that is disposed at an angle relative to a proximal portion of the blank that extends from the distal portion to the proximal end of the blank. The angle can be equal to about 30 degrees and a radius of curvature equal to about 0.20 inches can be disposed between the proximal portion and the distal portion. When forming the thread, the beginning of a thread lead out can be disposed at any suitable position along the length of the blank. For example, the beginning of a thread lead out can be disposed about 0.532 inches from a distal end of a blank when the blank has a length equal to about 0.591 inches. The tool path can include any suitable path capable of forming a thread, such as those described herein. For example, a tool path can extend from a proximal end of a blank at an inward angle of about 3 degrees relative to an axis that is parallel to the lengthwise axis of the blank to the beginning of a thread lead out, then parallel to the lengthwise axis of the blank, and then at an inward angle of about 7 degrees relative to an axis that is parallel to the lengthwise axis of the blank starting a distance from the distal end of the blank equal to about 0.180 inches.

FIGS. 26 and 27 illustrate an alternative screw 812 that can be included in a tissue anchor. The screw 812 is similar to the screw 712 illustrated in FIGS. 21, 22, 23, 24, and 25 and described above, except as detailed below. The screw 812 has a lengthwise axis 819, a screw main body 820, and a thread 822.

In the illustrated embodiment, the wall 834 extends from the screw proximal end 824 to the screw distal end 826 and defines a plurality of passageways 870. Each passageway of the plurality of passageways 870 extends through the wall 834, provides access to the lumen 832, and has an inside diameter 871 equal to about 0.042 inches. As shown in FIG. 26, a first set of passageways 872 of the plurality of passageways 870 is disposed on a first side 874 of the screw 812. As shown in FIG. 27, a second set of passageways 876 of the plurality of passageways 870 is disposed on a second side 878 of the screw 812. The first set of passageways 872 and the second set of passageways 876 is disposed on a plane that contains the lengthwise axis 819 of the screw 812. A first passageway 880 of the first set of passageways 872 is disposed a length 881 from the proximal end 824 of the screw 812 equal to about 0.119 inches. A second passageway 882 of the first set of passageways 872 is disposed a length 883 from the proximal end 824 of the screw 812 equal to about 0.279 inches. A third passageway 884 of the first set of passageways 872 is disposed a length 885 from the proximal end 824 of the screw 812 equal to about 0.437 inches. A first passageway 886 of the second set of passageways 876 is disposed a length 887 from the proximal end 824 of the screw 812 equal to about 0.079 inches. A second passageway 888 of the second set of passageways 876 is disposed a length 889 from the proximal end 824 of the screw 812 equal to about 0.238 inches. A third passageway 890 of the second set of passageways 876 is disposed a length 891 from the proximal end 824 of the screw 812 equal to about 0.399 inches. The inclusion of one or more passageways that extend through a wall of a screw is considered advantageous at least because it provides a mechanism for achieving bone ingrowth after implantation of the screw.

While screw 812 is illustrated as including a plurality of passageways 870 such that each passageway has a particular inside diameter and is disposed at a specific location on the screw, a screw can include any suitable number of passageways, having any suitable inside diameter, and positioned at any suitable location on the screw. Examples of numbers of passageways considered suitable to include on a screw include one, at least one, two, a plurality, three, four, five, six, seven, eight, nine, ten, more than ten, and any other number considered suitable for a particular embodiment. Examples of inside diameters considered suitable for a passageway included on a screw include diameters equal to, greater than, less than, or equal to 0.042 inches, between about 0.03 inches and about 0.05 inches, and any other diameter considered suitable for a particular embodiment. Examples of locations considered suitable to position a passageway, or set of passageways, include between a proximal end and a distal end of a screw, such that one or more passageways are disposed on a first plane that extends through a lengthwise axis of a screw and one or more passageways are disposed on a second plane that extends through the lengthwise axis of the screw that is coplanar with, or disposed at angle relative to the first plane that is equal to, greater than, less than, or about 90 degrees, 180 degrees, 270 degrees, between about 1 degree and about 359 degrees, and any other position considered suitable for a particular embodiment.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A tissue anchor comprising:
a screw having a lengthwise axis, a screw main body, and a thread extending from the screw main body and away from the lengthwise axis, the screw main body defining a first opening, a second opening, and a lumen extending from the first opening to the second opening; and
a stem releasably attached to the screw and partially disposed within the lumen defined by the screw, the stem having a stem proximal end, a stem distal end, and a stem main body defining a first portion, a second portion, a first recess, a second recess, a first passageway, a second passageway, and a first continuous surface, the first portion of the stem having a first portion proximal end, a first portion distal end disposed between the stem proximal end and the stem distal end, a first outside diameter, a first side, and a second side, the second portion of the stem having a second portion proximal end disposed between the stem proximal end and the stem distal end, a second portion distal end, a second portion length extending from the second portion proximal end to the second portion distal end, and a second outside diameter that is greater than the first outside diameter, each of the first recess and the second recess defined on the first portion of the stem and extending from the first portion proximal end to the first portion distal end, the first recess positioned on the first side of the first portion and the second recess positioned on the second side of the first portion, each of the first passageway and the second passageway extending through the entire second portion length, each of the first and second passageways extending only through the second portion and in communication with the lumen defined by the screw, each of the first and second passageways having an opening defined on the second portion proximal end, the first continuous surface extending from the first portion proximal end to the first portion distal end and defining a portion of the first passageway and the first recess.

2. The tissue anchor of claim 1, wherein the screw main body has a screw proximal end, a screw distal end, a distal portion extending from the screw distal end toward the screw proximal end, a third outside diameter at the screw proximal end, and a fourth outside diameter at the screw distal end that is less than the third outside diameter, the outside diameter of the screw main body tapering along the distal portion of the screw main body.

3. The tissue anchor of claim 1, wherein the thread has a thread length and a crest that is blunted along a portion of the thread.

4. The tissue anchor of claim 1, wherein the thread has a thread proximal end, a thread distal end, a thread length extending from the thread proximal end to the thread distal end, a first portion extending from the thread proximal end toward the thread distal end, a second portion extending from the first portion of the thread to the thread distal end, a pitch, and a height, the pitch being constant along the thread length, the height being constant along the first portion of the thread and tapering along the second portion of the thread.

5. The tissue anchor of claim 4, wherein the thread has a first side, a second side, and a thickness that extends from the first side of the thread to the second side of the thread, the thickness of the thread being constant along the first portion of the thread and tapering along the second portion of the thread.

6. The tissue anchor of claim 1, wherein the first recess has a first radius of curvature and the second recess has a second radius of curvature that is the same as the first radius of curvature.

7. The tissue anchor of claim 1, wherein the first portion of the stem has a first portion length; and wherein the second portion length is less than the first portion length.

8. The tissue anchor of claim 1, wherein each of the first passageway and the second passageway has an oval cross-sectional shape.

9. The tissue anchor of claim 1, wherein the first passageway is disposed adjacent to the first recess and the second passageway is disposed adjacent to the second recess.

10. The tissue anchor of claim 9, wherein the stem main body has a second continuous surface defining a portion of the second passageway and the second recess.

11. The tissue anchor of claim 1,
wherein the first passageway is disposed adjacent to the first recess;
wherein the second passageway is disposed adjacent to the second recess; and
wherein the first continuous surface defines the entire first recess.

12. A tissue anchor comprising:
a screw having a lengthwise axis, a screw main body, and a thread extending from the screw main body and away from the lengthwise axis, the screw main body having a screw proximal end, a screw distal end, a distal portion extending from the screw distal end toward the screw proximal end, a first outside diameter at the screw proximal end, and defining a first opening, a second opening, and a lumen extending from the first opening to the second opening, the outside diameter of the screw main body of the screw tapering along the distal portion of the screw main body, the thread having a thread proximal end, a thread distal end, a thread length extending from the thread proximal end to the thread distal end, a first portion extending from the thread proximal end toward the thread distal end, a second portion extending from the first portion of the thread to the thread distal end, a pitch, and a height, the pitch being constant along the thread length, the height being constant along the first portion of the thread and tapering along the second portion of the thread; and
a stem releasably attached to the screw and partially disposed within the lumen defined by the screw, the stem having a stem proximal end, a stem distal end, and a stem main body defining a first portion, a second portion, a first recess, a second recess, a first passageway, a second passageway, and a first continuous surface, the first portion of the stem having a first portion proximal end, a first portion distal end disposed between the stem proximal end and the stem distal end, a second outside diameter, a first side, and a second side, the second portion of the stem having a second portion proximal end disposed between the stem proximal end and the stem distal end, a second portion distal end, a second portion length extending from the second portion proximal end to the second portion distal end, and a third outside diameter that is greater than the second outside diameter, each of the first recess and the second recess defined on the first portion of the stem and extending from the first portion proximal end to the first portion distal end, the first recess positioned on the first side of the first portion of the stem and the second recess positioned on the second side of the first portion of the stem, each of the first passageway and the second passageway extending through the entire second portion length, each of the first and second passageways extending only through the second portion of the stem and in communication with the lumen defined by the screw, each of the first and second passageways having an opening defined on the second portion proximal end, the first continuous surface extending from the first portion proximal end to the first portion distal end and defining a portion of the first passageway and the first recess.

13. The tissue anchor of claim 12, wherein the thread has a first side, a second side, and a thickness that extends from the first side of the thread to the second side of the thread, the thickness of the thread being constant along the first portion of the thread and tapering along the second portion of the thread.

14. The tissue anchor of claim 12, wherein the first recess has a first radius of curvature and the second recess has a second radius of curvature, the first radius of curvature being the same as the second radius of curvature.

15. The tissue anchor of claim 12, wherein the first portion of the stem has a first portion length and the second portion of the stem has a second portion length that is less than the first portion length.

16. The tissue anchor of claim 12, wherein each of the first passageway and the second passageway has an oval cross-sectional shape.

17. The tissue anchor of claim 12, wherein the first passageway is disposed adjacent to the first recess and the second passageway is disposed adjacent to the second recess.

18. The tissue anchor of claim 17, wherein the stem main body has a second continuous surface defining a portion of the second passageway and the second recess.

19. A tissue anchor comprising:
a screw having a lengthwise axis, a screw main body, and a thread extending from the screw main body and away from the lengthwise axis, the screw main body having a screw proximal end, a screw distal end, a distal portion extending from the screw distal end toward the screw proximal end, a first outside diameter at the screw proximal end, and defining a first opening, a second opening, and a lumen extending from the first opening to the second opening, the outside diameter of the screw main body of the screw tapering along the distal portion of the screw main body, the thread having a thread proximal end, a thread distal end, a thread length extending from the thread proximal end to the thread distal end, a first portion extending from the thread proximal end toward the thread distal end, a second portion extending from the first portion of the thread to the thread distal end, a pitch, a height, a crest, a first side, a second side, and a thickness extending from the first side of the thread to the second side of the thread, the pitch being constant along the thread length, the height being constant along the first portion of the thread and tapering along the second portion of the thread, the crest being blunted along a portion of the thread, the thickness of the thread being constant along the first portion of the thread and tapering along the second portion of the thread; and a stem releasably attached to the screw and partially disposed within the lumen defined by the screw, the stem having a stem proximal end, a stem distal end, and a stem main body defining a first portion, a second portion, a first recess, a second recess, a first passageway, a second passageway, and a first continuous surface, the first portion of the stem having a first portion proximal end, a first portion distal end disposed between the stem proximal end and the stem distal end, a second outside diameter, a first side, and a second side, the second portion of the stem having a second portion proximal end disposed between the stem proximal end and the stem distal end, a second portion distal end, a second portion length extending from the second portion proximal end to the second portion distal end, and a third outside diameter that is greater than the second outside diameter, each of the first recess and the second recess defined on the first portion of the stem and extending from the first portion proximal end to the first portion distal end, the first recess positioned on the first side of the first portion of the stem and the second recess positioned on the second side of the first portion of the stem, each of the first passageway and the second passageway extending through the entire second portion length, each of the first and second passageways extending only through the second portion of the stem and in communication with the lumen defined by the screw, each of the first and second passageways having an opening defined on the second portion proximal end, the first passageway disposed adjacent to the first recess, the second passageway disposed adjacent to the second recess, the first continuous surface extending from the first portion proximal end to the first portion distal end and defining a portion of the first passageway and the first recess.

20. The tissue anchor of claim 19, wherein the stem main body of the stem has a second continuous surface defining a portion of the second passageway and the second recess.

* * * * *